US009102742B2

(12) United States Patent
Semenova et al.

(10) Patent No.: US 9,102,742 B2
(45) Date of Patent: Aug. 11, 2015

(54) SEROLOGIC CORRELATES OF PROTECTION AGAINST *BACILLUS ANTHRACIS* INFECTION

(71) Applicant: Centers for Disease Control and Prevention, Atlanta, GA (US)

(72) Inventors: Vera A. Semenova, Lilburn, GA (US); Conrad P. Quinn, Lilburn, GA (US); Jan Pohl, Tucker, GA (US); Pavel Svoboda, Atlanta, GA (US); Shannon Dalton, Stone Mountain, GA (US); Jarad M. Schiffer, Atlanta, GA (US)

(73) Assignee: The United States of America as represented by the Secretary, Department of Health and Human Services, Centers for Disease Control and Prevention, Washington, DC (US)

( * ) Notice: Subject to any disclaimer, the term of this patent is extended or adjusted under 35 U.S.C. 154(b) by 6 days.

(21) Appl. No.: 14/010,668

(22) Filed: Aug. 27, 2013

(65) Prior Publication Data
US 2014/0004139 A1    Jan. 2, 2014

Related U.S. Application Data

(63) Continuation-in-part of application No. 13/577,878, filed as application No. PCT/US2011/024317 on Feb. 10, 2011.

(60) Provisional application No. 61/333,456, filed on May 11, 2010, provisional application No. 61/303,055, filed on Feb. 10, 2010.

(51) Int. Cl.
G01N 33/554    (2006.01)
C07K 14/32    (2006.01)
G01N 33/569    (2006.01)

(52) U.S. Cl.
CPC .......... *C07K 14/32* (2013.01); *G01N 33/56911* (2013.01)

(58) Field of Classification Search
USPC ............. 435/7.1, 7.2, 7.32; 424/246.1, 234.1, 424/190.1
See application file for complete search history.

(56) References Cited

U.S. PATENT DOCUMENTS

| | | | |
|---|---|---|---|
| 4,196,191 A | 4/1980 | Almeida et al. | |
| 4,215,051 A | 7/1980 | Schroeder et al. | |
| 6,017,513 A | 1/2000 | Betbeder et al. | |
| 6,368,602 B1 | 4/2002 | Gilad et al. | |
| 6,541,030 B2 | 4/2003 | Vaghefi | |
| 6,544,646 B2 | 4/2003 | Vaghefi et al. | |
| 6,663,861 B2 | 12/2003 | Hansen et al. | |
| 6,846,917 B2 | 1/2005 | Seeberger et al. | |
| 6,979,456 B1 | 12/2005 | Parikh et al. | |
| 7,041,705 B2 | 5/2006 | Mishra et al. | |
| 7,097,849 B2 | 8/2006 | Mishra et al. | |
| 7,201,912 B2 | 4/2007 | Park et al. | |
| 2004/0076638 A1 | 4/2004 | Shiloach et al. | |

FOREIGN PATENT DOCUMENTS

| | | |
|---|---|---|
| WO | WO-2005068493 A1 | 7/2005 |
| WO | WO 2005068493 A1 * | 7/2005 |
| WO | WO-2007/131363 A1 | 11/2007 |
| WO | WO-2011100408 A2 | 8/2011 |
| WO | WO-2013022808 A2 | 2/2013 |
| WO | WO-2013063366 A2 | 5/2013 |

OTHER PUBLICATIONS

Singer, Darrell E. et al., Serum IgG antibody response to the protective antigen (PA) of *Bacillus anthracis* induced by U.S. military personnel; Vaccine, Feb. 2008, vol. 26., No. 7., pp. 869-873.
Quinn, Conrad P. et al.; Immune Responses to *Bacillus anthracis* Protective Antigen in Patients with Bioterroism-Related Cutaneous or Inhalation Anthrax; Journal of Infectious Disease; 2004; vol. 190; pp. 1228-1236.
Chothia et al., "The relation between the divergence of sequence and structure in proteins," The EMBO Journal, vol. 5, No. 4, pp. 823-826, 1986.
Mikayama et al., Proc. Natl. Acad. Sci USA, vol. 90: 10056-10060, Nov. 1993).
Rudinger et al., Peptide Hormones, Biol. Council, pp. 5-7, Jun. 1976.
Abbas et al., Cellular and Molecular Immunology, 4th edition, Ch. 15, p. 360-362, 2000.
Abboud, et al., "Identification of Linear Epitopes in *Bacillus anthracis* Protective Antigen Bound by Neutralizing Antibodies," J. Biol. Chem. 2009, 284:25077-25086.
Baudner, et al., "Enhancement of Protective Efficacy following Intranasal Immunization with Vaccine Plus a Nontoxis LTK63 Mutant Delivered with Nanoparticles," Infection and Immunity, vol. 70, No. 9, Sep. 2002, p. 4785-4790.
Brady, et al., "Analysis of Antibody Responses to Protective Antigen-Based Anthrax Vaccines through Use of Competitive Assays," Clin. Vaccine Immunol., 2010, 17(9):1390.

(Continued)

*Primary Examiner* — Jennifer Graser
(74) *Attorney, Agent, or Firm* — Gifford, Krass, Sprinkle, Anderson & Citkowski, P.C.; Weston R. Gould

(57) ABSTRACT

Regions of *B. anthracis* protective antigen are provided representing sequences recognized by antibodies in subjects that have vaccine induced lethal toxin neutralizing anti-PA IgG responses. The recognition of these PA regions enhances the utility of anti-PA IgG reactivity as an immune correlate of protection against anthrax in a subject and increases predictive probability of survival. Also provided are vaccines that include at least one of these PA regions that when administered to a subject improve the predictive value of vaccine induced anti-PA IgG and TNA responses as immune correlates of protection against inhalation anthrax.

18 Claims, 12 Drawing Sheets

(56) References Cited

OTHER PUBLICATIONS

Brossier, et al., "Toxins of *Bacillus anthracis*," Toxicon 39 (2001) 1747-1755.

Castignolles, et al., "A new family of carriers (biovectors) enhances the immunogenicity of rabies antigens," Vaccine, vol. 14, No. 14, pp. 1353-1360 (1996).

Crowe, S., et al., "Select Human Anthrax Protective Antigen Epitope-Specific Antibodies Provide Protection from Lethal Toxin Challenge," J. Infect. Diseases, 2010, 202(2), pp. 251-260.

Delong, E., et al., "Comparing the Areas under Two or More Correlated Receiver Operating Characteristic Curves: A Nonparametric Approach," Biometrics, vol. 44, No. 3 (Sep. 1988), pp. 837-845.

Dumas, ET. et al., "Stochastic humoral immunity to *Bacillus anthracis* protective antigen: Identification of anti-peptide IgG correlating with seroconversion to Lethal Toxin neutralization," Vaccine 31 (2013) 1856-1863.

El Guink, N. et al., "Intranasal immunization with proteoliposomes protects against influenza," Vaccine, vol. 7, Apr. 1989, pp. 147-151.

Friedman, J., et al., "Regularization Paths for Generalized Linear Models via Coordinate Descent," J Stat Softw. 2010; 33(1): 1-22.

Greenspan, N. et al., "Defining epitopes: It's not as easy as it seems," Nature Biotechnology, vol. 17, Oct. 1999, pp. 936-937.

Hackeng, T., et al., "Total chemical synthesis of enzymatically active human type II secretory phospholipase $A_2$," Proc. Natl. Acad. Sci. USA, vol. 94, pp. 7845-7850, Jul. 1997.

Kaur, M. et al., Identification and characterization of immunodominant B-cell epitope of the C-terminus of protective antigen of *Bacillus anthracis*, Molecular Immunology 46 (2009) 2107-2115.

Kelly-Cirino, C., et al., "Neutralizing Monoclonal Antibodies Directed against Defined Linear Epitopes on Domain 4 of Anthrax Protective Antigen," Infection and Immunity, vol. 77, No. 11, Nov. 2009, p. 4859-4867.

Kochendoerfer, G., "Chemical protein synthesis methods in drug discovery," Current Opinion in Drug Discovery & Development, 2001, vol. 4, No. 2, pp. 205-214.

Major, M., et al., "Characterisation and phase behaviour of phospholipid bilayers adsorbed on spherical polysaccharidic nanoparticle", Biochemica et Biophysica Acta, 1327 (1997) pp. 32-40.

Miranda, L., et al., "Challenges for Protein Chemical Synthesis in the 21st Century: Bridging Genomics and Proteomics," Biopolymers (Peptide Science), vol. 55, 217-226 (2000).

Mock, M. et al., "Anthrax toxins and the host: a story of intimacy," Cellular Microbiology, 5(1), 15-23 (2003).

Oscherwitz, J. et al., "Synthetic Peptide Vaccine Targeting a Cryptic Neutralizing Epitope in Domain 2 of *Bacillus anthracis* Protective Antigen," Infect. Immun. 2009, 77(8): 3380.

Oscherwitz, J., et al., "A Synthetic Peptide Vaccine Directed against the 2β2-2β3 Loop of Domain 2 of Protective Antigen Protects Rabbits from Inhalation Anthrax," J Immunol 2010; 185:3661-3668.

Prieur, E., et al., Combination of human cytomegalovirus recombinant immediate-early protein (IE1) with 80nm cationic biovectors: protection from proteolysis and potentiation of presentation to CD4+ T-cell clones in vitro, Vaccine, vol. 14, No. 6, pp. 511-520, 1996.

Quiinn, C. et al., "A Three-Dose Intramuscular Injection Schedule of Anthrax Vaccine Adsorbed Generates Sustained Humoral and Cellular Immune Responses to Protective Antigen and Provides Long-Term Protection against Inhalation Anthrax in *Rhesus macaques*," Clinical and Vaccine Immunology, vol. 19, No. 11, Nov. 2012, pp. 1730-1745.

Reason, D. et al., "Frequency and Domain Specificity of Toxin-Neutralizing Paratopes in the Human Antibody Response to Anthrax Vacine Adsorbed," Infect. Immun., May 2009, 77(5): 2030-2035.

Semenova V., et al., "Antigenic Peptides of Anthrax Toxin PA Stimulate Lethal Toxin Neutralizing Responses in Mice," ASM Abstract, 2012.

Smith, K., et al., "Human monoclonal antibodies generated following vaccination with AVA provide neutralization by blocking furin cleavage but not by preventing oligomerization," Vaccine, 30 (2012) 4276-4283.

International Search Report and Written Opinion for co-pending PCT Application No. PCT/US2014/052895, issued Dec. 12, 2014.

\* cited by examiner

SEROLOGIC CORRELATES OF PROTECTION AGAINST *BACILLUS ANTHRACIS* INFECTION

CROSS REFERENCE TO RELATED APPLICATIONS

This application is a continuation-in-part of U.S. application Ser. No. 13/577,878, filed Aug. 8, 2012, which is the U.S. National Stage of application PCT/US2011/024317 filed Feb. 10, 2011, and which claims priority to U.S. Provisional Application No. 61/303,055 filed Feb. 10, 2010, and U.S. Provisional Application No. 61/333,456 filed May 11, 2010, the contents of each of which are incorporated herein by reference.

GOVERNMENT INTEREST

The invention described herein may be manufactured, used, and licensed by or for the United States Government.

FIELD OF THE INVENTION

The invention relates to physiologically relevant epitope sequences related to acquired immunity to *Bacillus anthracis* protective antigen (PA). The peptide sequences of the invention represent previously unidentified regions of PA that elicit an immune response in a mammal. Particularly, the invention presents epitopes targeted by the immune system in rhesus macaques following immunization with compounds and formulations containing or producing anthrax toxin protective antigen (PA).

BACKGROUND OF THE INVENTION

Anthrax is caused by infection with *Bacillus anthracis*, a spore-forming, rod-shaped bacterium. The dormant spore-form is highly resistant to extreme conditions, high temperatures, and a variety of chemical treatments. The spores gain entry either through an open wound causing cutaneous disease, by ingestion causing gastrointestinal disease, by injection, or are inhaled causing inhalation anthrax. All three forms can progress to a systemic infection leading to shock, respiratory failure, and death. (Mock, M. and Mignot, T, (2003) *Cell Microbiol.*, 5(1):15-23). The stability of the spores, and their infectious capacity, make them a convenient bioterrorist weapon.

Two of the known toxins of *B. anthracis* are binary combinations of protective antigen (PA), named for its ability to induce protective immunity against anthrax, with either edema factor (EF) or lethal factor (LF). PA is the cell biding component of both toxins and is responsible for bringing the catalytic EF or LF into the host cells. EF is an adenylate cyclase which converts ATP to cyclic AMP and causes edema (Brossier, F. & Mock, M, 2001, *Toxicon.* 39 (11):1747-55). The combination of PA-EF forms edema toxin (ETx) which causes edema when injected locally. LF is a zinc-dependent endoprotease known to target the amino-terminus of the mitogen-activated protein kinase kinase (MAPKK) family of response regulators (Id.). The cleavage of these proteins disrupts a signaling pathway and leads to cytokine dysregulation and immune dysfunction. LF combined with PA forms lethal toxin (LTx) which is lethal in some animal models when injected on its own. It is also known that there are fatal anthrax cases where administration of antibiotics and clearance of bacteria have failed to rescue the patient. This indicates that there may be a "point of no return" level of LTx in the blood that may predict the outcome of infection.

Development of a safe and effective vaccine for inhalation and other forms of anthrax is vital to the health and safety of the population and an essential component of an anthrax bioterrorism defense strategy. Additionally, the identification of targeted therapies following *B. anthracis* infection is essential to managing a patient population. As such, there exists a need for vaccines and treatments as well as methods for determining whether post-vaccination protection is achieved prior to possible *B. anthracis* exposure and infection.

SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

A process of determining protection against *B. anthracis* infection or complications therefrom in a subject is provided that includes obtaining a biological sample from a subject, optionally after a first onset time, and screening the biological sample for the presence or absence of antibodies to one or more predefined regions of *B. anthracis* protective antigen (PA). A predefined region is 5 or more amino acid residues, or other epitope region length, of amino acids 561-590 or 681-710 of mature *B. anthracis* protective antigen. The presence or absence of these antibodies allows one to enhance the utility of anti-PA IgG reactivity and lethal toxin neutralization activity (TNA) as an immune correlate of protection against *B. anthracis*. Some embodiments include a prior administration of a *B. anthracis* vaccine that may be the anthrax vaccine adsorbed (AVA) vaccine, a recombinant or other protective antigen sequence, or an immunogenic fragment of protective antigen such as an immunogen corresponding to amino acid regions 121-150, 201-230, 221-250, 241-270, 301-330, 321-350, 341-370, 361-390, 421-450, 541-570; 561-590, 641-670, or 681-710 of *B. anthracis* protective antigen, or any immunogenic fragment thereof, or any combination thereof, to the subject prior to obtaining the biological sample. A subject is optionally vaccinated with an AVA vaccine or a recombinant protective antigen vaccine including nucleic acid vaccines or live attenuated vector vaccines comprised or expressing coding sequences corresponding to the amino acid regions.

The predefined region of *B. anthracis* protective antigen is optionally at least one of the amino acid region of 41-70, 121-150, 201-230, 221-250, 241-270, 301-330, 321-350, 341-370, 361-390, 421-450, 541-570, 561-590, 641-670, or 681-710 of SEQ ID NO: 1, or any combination thereof, or any immunogenic fragment thereof, or combination of immunogenic fragments.

A process optionally includes a second administering of the same or a different vaccine, obtaining a second biological sample following a second onset time, and screening the second biological sample for the presence or absence of antibodies to one or more predefined regions of *B. anthracis* protective antigen. The presence or level of protection against *B. anthracis* is then determined from the screening of the second biological sample.

Also provided is a process of eliciting an immune response in a subject including administering a *B. anthracis* vaccine including an immunogen corresponding to amino acid regions 41-70, 121-150, 201-230, 221-250, 241-270, 301-

330, 321-350, 341-370, 361-390, 421-450, 541-570; 561-590, or 641-670 of SEQ ID NO: 1, an immunogenic fragment thereof, or any combination thereof, to a subject. A vaccine is optionally an isolated immunogen corresponding to amino acid regions 41-70, 121-150, 201-230, 221-250, 241-270, 301-330, 321-350, 341-370, 361-390, 421-450, 541-570; 561-590, or 641-670 of SEQ ID NO: 1, a fragment thereof, or any combination thereof. The immune response is optionally the production of antibodies specific to *B. anthracis* protective antigen. The antibodies optionally neutralize lethal toxin.

Also provided is a vaccine that will produce acquired immunity to *B. anthracis* infection that includes an isolated immunogen corresponding to amino acid regions 41-70, 121-150, 201-230, 221-250, 241-270, 301-330, 321-350, 341-370, 361-390, 421-450, 541-570; 561-590, or 641-670 of SEQ ID NO: 1, a fragment thereof, or any combination thereof. A vaccine optionally includes amino acid regions of *B. anthracis* protective antigen.

DETAILED DESCRIPTION OF EMBODIMENTS OF THE INVENTION

Figure 1:
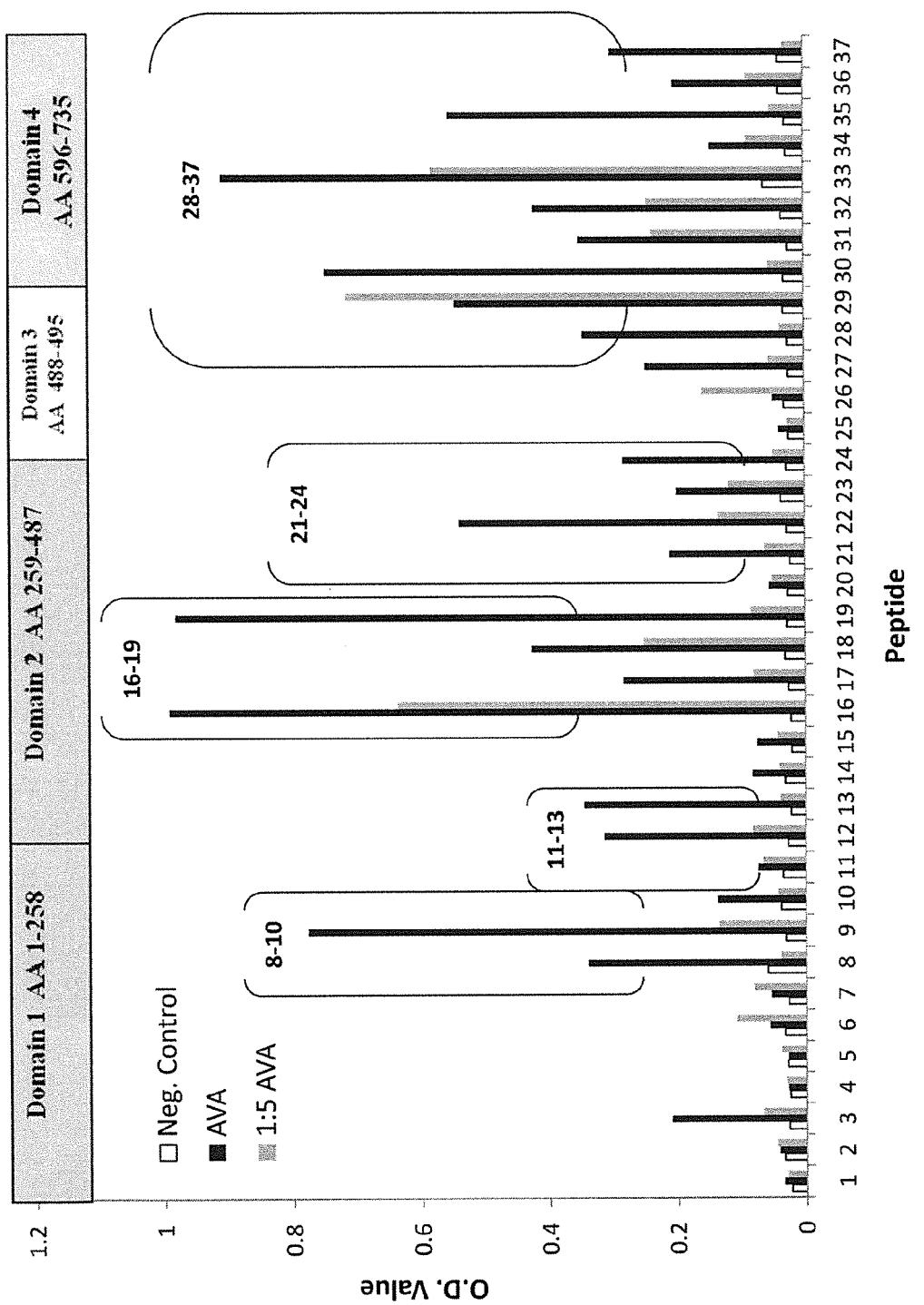
FIG. 1 represents the reactivity of sera from AVA vaccinated rhesus macaques with peptides representing overlapping sequences of protective antigen.
Figure 2:
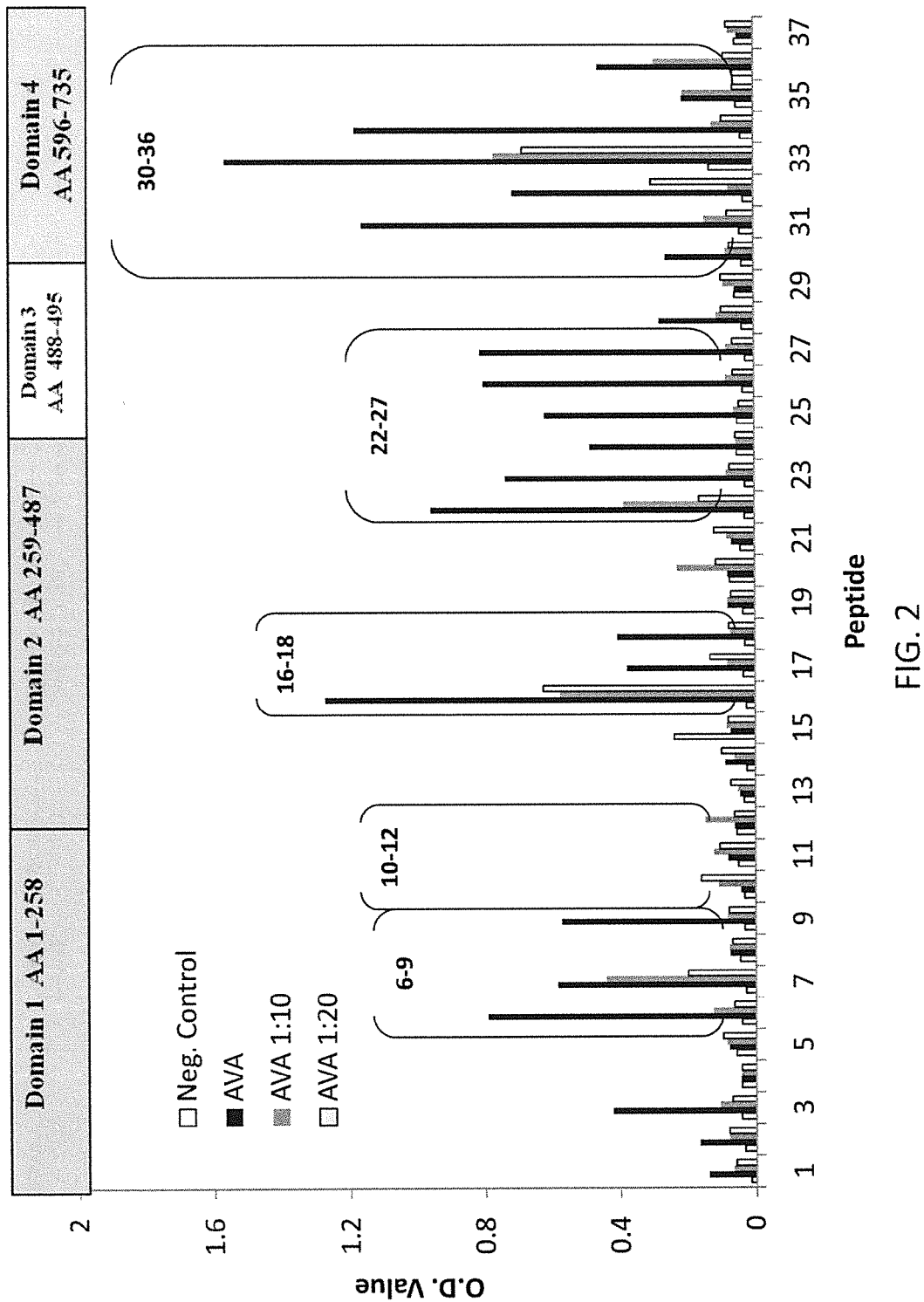
FIG. 2 represents the reactivity of sera from AVA vaccinated rabbits with peptides representing overlapping sequences of protective antigen.
Figure 3:
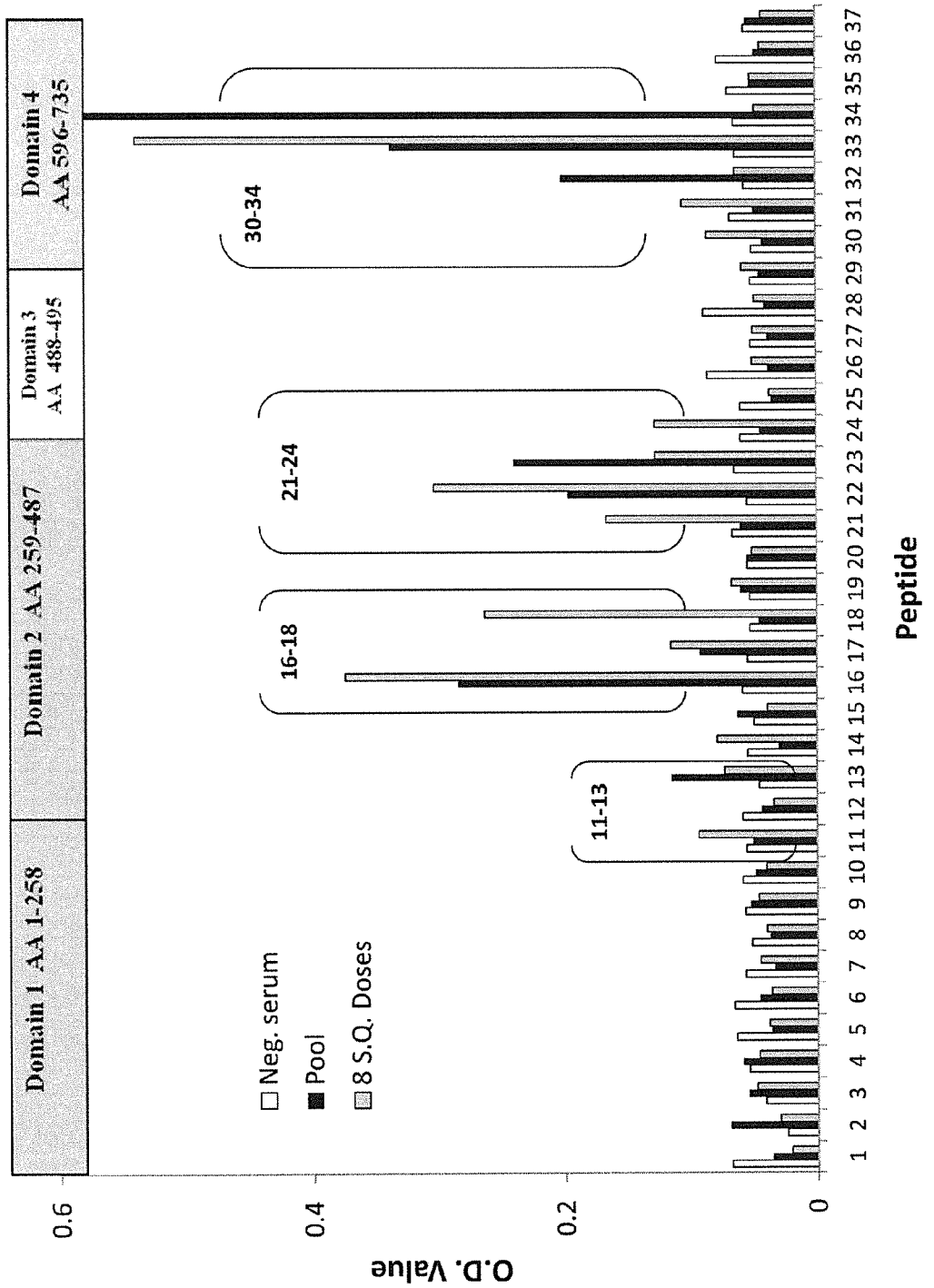
FIG. 3 represents the reactivity of sera from AVA vaccinated humans with peptides representing overlapping sequences of protective antigen.
Figure 4:
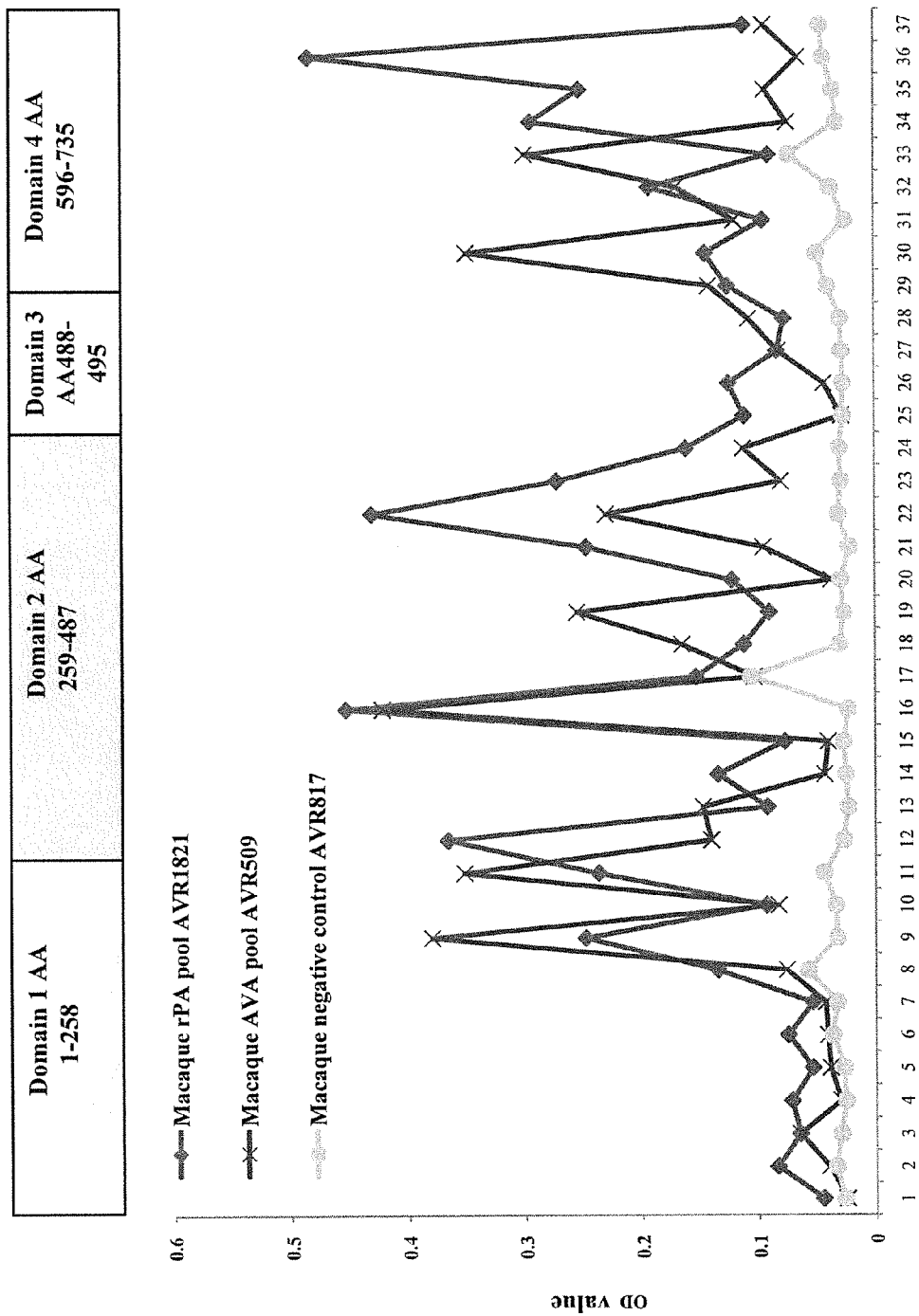
FIG. 4 represents the regions of PA recognized by antibodies from rhesus macaque sera vaccinated with either AVA or purified rPA.
Figure 5:
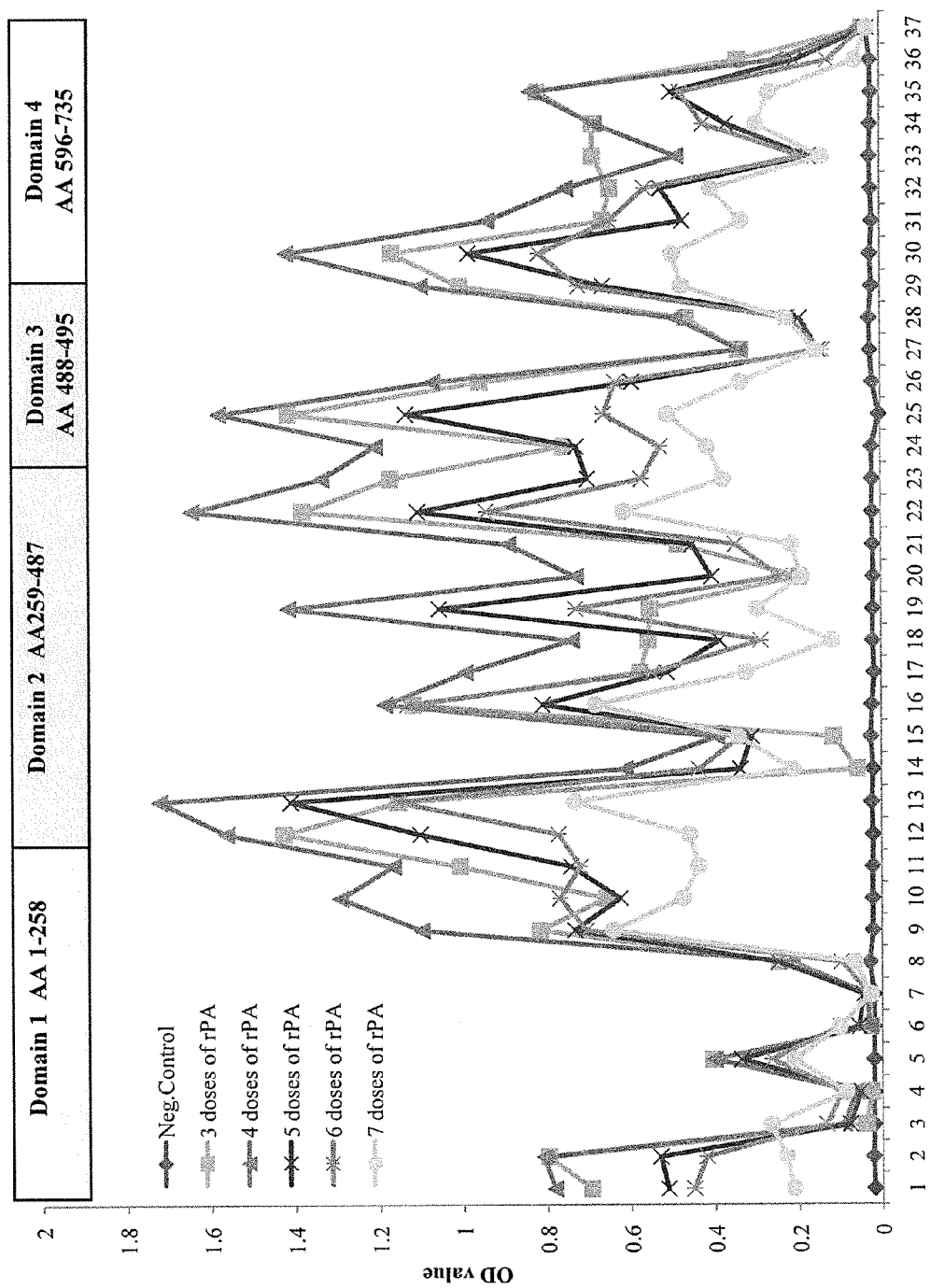
FIG. 5 represents the reactivity of sera from macaques that received 50 μg of rPA at 0, 2, 4, 8, 12, 16 and 20 weeks where the screening was done after administration of each injection starting from $3^{rd}$ dose till $7^{th}$ dose of rPA.

The following description of particular embodiment(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only.

The invention has utility as a predictor of immunity to *B. anthracis* infection. The invention has further utility as one or more peptide sequences that alone or when combined are improved vaccines conferring protection against *B. anthracis* infection in a subject.

The invention provides polypeptide sequences that include relevant epitopes recognized by antibodies from subjects with acquired immunity to *B. anthracis* infection. The polypeptide sequences alone or in combination are useful for enhancing serologic correlates of protection to subsequent *B. anthracis* infection.

As such, a process for identifying or predicting immunity to infection by *B. anthracis* is provided including screening for antibodies in a sample obtained from a subject following vaccination with rPA, AVA, or fragments thereof, or prior infection by *B. anthracis*, to identify whether antibodies to predefined regions of PA are generated by or present in the subject. The presence or absence of antibodies to one or more predefined regions of PA generates protective immune responses against subsequent infection by *B. anthracis*. Standard vaccines for *B. anthracis* often require multiple administrations to produce the desired level of immunity. The processes of the invention provide a mechanism by which a physician can identify whether a particular subject needs additional vaccine administrations or has already developed the necessary protection against subsequent infection by *B. anthracis*. The binding of antibodies from a subject to one or more predefined regions of PA indicates the presence of acquired immunity and enhances immune correlates of protection (COP) against inhalation anthrax in Anthrax Vaccine Adsorbed (AVA) vaccinated rhesus macaques (nonhuman primates; NHP).

As defined herein, a "predefined region" is a region of PA at least a portion of which serves as a B-cell epitope. A predefined region is a region of PA, optionally having 30 amino acids or fewer, that is recognized by antibodies from subjects with immunity to *B. anthracis* infection. A predefined region includes a B-cell epitope or immunogenic portion thereof. As such, a predefined region may be termed an epitope, but it is appreciated that a predefined region may include additional non-epitope amino acids or be limited to the epitope region itself. It is also appreciated that the epitope present within one of the sequences listed herein is the essential and minimal sequence necessary. As such, the listing of predefined regions herein are appreciated to be a region experimentally determined to include the essential epitope, but the invention need not include the entire sequence of each predefined region as listed herein as long as the epitope for the antibodies targeting each predefined region are included, or conservative mutations of amino acids therein.

A predefined region is optionally one or more of the following regions of PA: the calcium ion chelating residues in the $1\alpha_1$ and $1\beta_{13}$ strands, (AA181-210); $1\beta_{13}$, $1\alpha_2$, $1\beta_{14}$ (AA201-230); $1\alpha_3$ and $1\alpha_4$ (AA 221-250); and $1\alpha_4$ and $2\beta_1$ (AA241-270) regions in domain 1; the chymotrypsin sensitive loop $2\beta_2$-$2\beta_3$ (AA 301-330); $2\beta_3$ and $2\alpha_1$ (AA 321-350); $2\alpha_1$, $2\beta_4$ and $2\beta_5$ (AA341-370); $2\beta_6$ and $2\beta_7$ (AA361-390); $2\beta_{10}$, $2\beta_{11}$, $2\alpha_2$ and $2\beta_{12}$ (AA421-450); $2\beta_{13}$ in domain 2, $3\alpha_3$, $3\alpha_4$ (AA 561-590); and $3\beta_7$, $3\beta_8$ (AA581-610) in domain 3 and partially in domain 4 of PA; fragments thereof; or combinations thereof.

A process optionally includes screening for antibodies to more than one predefined region. Screening is optionally performed following a single administration of vaccine. Optionally, screening is done after several vaccinations. Optionally, screening is done after each of several vaccinations. Optionally, screening is done no more than one time. Illustratively, a subject is vaccinated with PA, recombinant PA, AVA, a vaccine as provided by the current invention, and/or other vaccine known in the art intended to provide immunity against *B. anthracis* infection, once, three times, five times, or more and a biological sample such as blood is obtained from the subject for determination of the presence or absence of antibodies to predefined regions of PA. Recognition of one or more antibodies to one or more predefined regions of PA following vaccination correlates with a predicted level of protection to subsequent infection by *B. anthracis*.

As used herein, the term "anthrax" is intended to mean *B. anthracis*. As such, a subject suffering from anthrax is infected by *B. anthracis*. Similarly, anthrax such as virulent anthrax is the organism *B. anthracis*.

strongly correlate with acquired immunity to virulent anthrax because even though the structural region containing this loop may be important immunologically as a T cell epitope, recipients of vaccines such as AVA and rPA may not recognize this region as an antibody reactive B cell epitope. (Oscherwitz J, et al., *Infect Immun*, 2009; 77 (8):3380-8.) As such, this region of PA was not expected to be a good correlate of immunity. The presence of antibodies to this and surrounding regions of PA in multiple species as identified in the present invention surprisingly demonstrates its importance as a correlate of immunity.

Antibody screening is accomplished by methods known in the art, illustratively, enzyme linked immunosorbent assay (ELISA), affinity chromatography, liquid chromatography, or other methods appreciated by those of ordinary skill in the art. In some embodiments, a sample is obtained from a subject and screened in an ELISA assay using one or more peptides representing epitopes in PA or non-epitope regions. A positive result is the presence of one or more antibodies in the sample to one or more epitopes above background levels, optionally 2 times background, optionally 3 times background. In some embodiments, an amino acid sequence from each of the four domains of PA, domain 1 (aa 1-258), domain 2 (aa 25-487), domain 3 (aa 488-595), and/or domain 4 (aa 596-735) are represented by at least one peptide. It is appreciated that the numbering of predefined sequences represents the numbering of the mature PA sequence. PA such as that illustrated in SEQ ID NO: 1, is free of the putative signal sequence of 29 amino acids that is cleaved to produce the mature PA protein. As such, the numbering presented herein is related to mature PA.

The inventive epitope containing regions are peptide regions of PA from *B. anthracis* (SEQ ID NO: 1).

```
                                                                (SEQ ID NO: 1)
EVKQENRLLNE SESSSQGLLG YYFSDLNFQA PMVVTSSTTG DLSIPSSELE

NIPSENQYFQ SAIWSGFIKV KKSDEYTFAT SADNHVTMWV DDQEVINKAS

NSNK1RLEKG RLYQIKIQYQ RENPTEKGLD FKLYWTDSQN KKEVISSDNL

QLPELKQKSS NSRKKRSTSA GPTVPDRDND GIPDSLEVEG YTVDVKNKRT

FLSPWISNIH EKKGLTKYKS SPEKWSTASD PYSDFEKVTG RIDKNVSPEA

RHPLVAAYPI VHVDMENIIL SKNEDQSTQN TDSQTRTISK NTSTSRTHTS

EVHGNAEVHA SFFDIGGSVS AGFSNSNSST VAIDHSLSLA GERTWAETMG

LNTADTARLN ANIRYVNTGT APIYNVLPTT SLVLGKNQTL ATIKAKENQL

SQILAPNNYY PSKNLAPIAL NAQDDFSSTP ITMNYNQFLE LEKTKQLRLD

TDQVYGNIAT YNFENGRVRV DTGSNWSEVL PQIQETTARI IFNGKDLNLV

ERRIAAVNPS DPLETTKPDM TLKEALKIAF GFNESNGNLQ YQGKDITEFD

FNFDQQTSQN IKNQLAELNV TNIYTVLDKI KLNAKMNILI RDKRFHYDRN

NIAVGADESV VKEAHREVIN SSTEGLLLNI DKDIRKILSG YIVEIEDTEG LKEVINDRYD

MLNISSLRQD GKTFIDFKKY NDKLPLYISN PNYKVNVYAV TKENTIINPS

ENGDTSTNGI KKILIFSKKG YEIG
```

Interestingly, and in contrast to results expected from the prior art, the chymotrypsin sensitive loop $2\beta_2$-$2\beta_3$ presents a strong epitope in PA that is found following vaccination in humans, rabbits, and rhesus macaques. The $2\beta_2$-$2\beta_3$ loop is involved in the transition of PA oligomers from prepore to pore. This region was not expected to show strong antigenicity in each of humans, rabbits, and Rhesus macaques, and to Optionally, a predefined region of PA useful to as a correlate of protection includes but is not limited to: mature PA residues 41-70, the calcium ion chelating residues in the $1\alpha_1$ and $1\beta_{13}$ strands, (AA181-210); $1\beta_{13}$, $1\alpha_2$, $1\beta_{14}$ (AA201-230); $1\alpha_3$ and $1\alpha_4$ (AA221-250); and $1\alpha_4$ and $2\beta_1$ (AA241-270) regions in domain 1; the chymotrypsin sensitive loop $2\beta_2$-$2\beta_3$ (AA 301-330); $2\beta_3$ and $2\alpha_1$ (AA 321-350); $2\alpha_1$, $2\beta_4$ and 2$\beta_5$ (AA341-370); 2$\beta_6$ and 2$\beta_7$ (AA361-390); 2$\beta_{10}$, 2$\beta_{11}$, 2$\alpha_2$ and 2$\beta_{12}$ (AA421-450); 2$\beta_{13}$ in domain 2, 3$\alpha_3$, 3$\alpha_4$ (AA 561-590); and 3$\beta_7$, 3$\beta_8$ (AA581-610) in domain 3 and partially in domain 4 of PA; mature PA residues 641-670; mature PA residues 681-710; mature PA residues 121-150; immunogenic fragments thereof; or combinations thereof.

Optionally, a predefined region that serves as a correlate of protection is mature PA residues 41-70 representing peptide 3 and having an amino acid sequence of GDLSIPSSELENI-PSENQYFQSAIWSGFIK (SEQ ID NO: 14) or an immunogenic portion thereof. This predefined region shows weak positive correlation to acquired immunity to B. anthracis alone, but as a portion of a collection of predefined regions contributes to significant positive correlation to protection.

Optionally, a predefined region that serves as a correlate of protection is in the 2$\beta_2$-2$\beta_3$ region of mature PA in a peptide having residues 301-330 representing peptide 16 and having an amino acid sequence of SEVHGNAEVHASFFDIGGS-VSAGFSNSNSS (SEQ ID NO: 3) or an immunogenic portion thereof. This predefined region shows positive correlation to acquired immunity to B. anthracis.

Optionally, a predefined region that serves as a correlate of protection is mature PA residues 401-430 representing peptide 21 and having an amino acid sequence of LSQILAPN-NYYPSKNLAPIALNAQDDFSST (SEQ ID NO: 15) or an immunogenic portion thereof. This predefined region shows positive correlation to acquired immunity to B. anthracis.

Optionally, a predefined region that serves as a correlate of protection is mature PA residues 561-590 representing peptide 29 and having an amino acid sequence of NIKNQLAEL-NVTNIYTVLDKIKLNAKMNIL (SEQ ID NO: 13) or an immunogenic portion thereof. This predefined region shows positive correlation to acquired immunity to B. anthracis.

Optionally, a predefined region that serves as a correlate of protection is mature PA residues 641-670 representing peptide 33 and having an amino acid sequence of GYIVEIEDTEGLKEVINDRYDMLNISSLRQ (SEQ ID NO: 16) or an immunogenic portion thereof. This predefined region shows positive correlation to acquired immunity to B. anthracis.

Optionally, a predefined region that serves as a correlate of protection is mature PA residues 561-590 representing peptide 29 and having an amino acid sequence of NIKNQLAEL-NVTNIYTVLDKIKLNAKMNIL (SEQ ID NO: 12) or an immunogenic portion thereof. This predefined region shows positive correlation to acquired immunity to B. anthracis.

Optionally, a predefined region that serves as a correlate of protection is mature PA residues 681-710 representing peptide 35 and having an amino acid sequence of YNDKLPLY-ISNPNYKVNVYAVTKENTIINP (SEQ ID NO: 17) or an immunogenic portion thereof. This predefined region shows negative correlation to acquired immunity to B. anthracis.

It is appreciated that peptide numbering is readily obtained from the mature PA sequence of SEQ ID NO: 1 as each peptide is a 30 amino acid sequence of mature PA beginning at residue 1 and overlapping by 10 amino acids. Thus, a sequence referred to herein as a peptide is readily understood on the basis of amino acid sequence.

An inventive process optionally includes obtaining a biological sample from a subject; screening the biological sample for the presence or absence of antibodies to one or more predefined regions of B. anthracis protective antigen, at least one of said predefined regions comprising residues 641-670 (peptide 33) or 681-710 (peptide 35) of mature B. anthracis protective antigen or an immunogenic portion thereof; and determining the level of protection against B. anthracis from the screening.

As used herein a "subject" is a mammal. Optionally, a subject is a human or non-human primate. Optionally, a subject is a dog, cat, equine, sheep, bovine, rabbit, pig, or murine.

As used herein, the term "biological sample" is defined as sample obtained from a biological organism, a tissue, cell, cell culture medium, or any medium suitable for mimicking biological conditions, or from the environment. Non-limiting examples include saliva, gingival secretions, cerebrospinal fluid, gastrointestinal fluid, mucous, urogenital secretions, synovial fluid, blood, serum, plasma, urine, cystic fluid, lymph fluid, ascites, pleural effusion, interstitial fluid, intracellular fluid, ocular fluids, seminal fluid, mammary secretions, vitreal fluid, nasal secretions, throat or nasal materials, and combinations thereof. It is appreciated that a biological sample is optionally a cell, illustratively, cells of or related to the immune system. Cells illustratively include white blood cells. Illustrative examples of white blood cells include leukocytes such as T-cells, B-cells, and T-helper cells.

A biological sample is obtained from a subject by conventional techniques. For example, CSF is obtained by lumbar puncture. Blood is optionally obtained by venipuncture, while plasma and serum are optionally obtained by fractionating whole blood according to known methods.

A process includes screening the biological sample for the presence or absence of antibodies to one or more predefined regions of mature PA or an immunogenic portion thereof. Antibodies are appreciated to be any suitable antibody type illustratively including IgG, IgM, IgA, IgE, or other. Optionally, antibodies of the IgG type are targeted. A biological sample is screened optionally using a peptide encompassing a predefined region of mature PA using conventional techniques. Illustratively, an enzyme linked immunosorbent assay (ELISA) is used. It is appreciated that other techniques known in the art are similarly suitable.

In some embodiments, the step of screening includes contacting a plurality of screening peptides with said sample such that specific binding of an immunoglobulin to one or more of said peptides is detectable. A screening peptide is optionally a predefined region, includes a predefined region, or is an immunogenic portion of a predefined region. A screening peptide includes from 5 to 40 amino acids, or any value or range therebetween. Optionally, a screening peptide includes 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 residues. A peptide is not full length mature or immature PA. A plurality of peptides optionally are of overlapping sequence, or of non-overlapping sequences. Peptides are optionally labeled. A label is optionally biotin, streptavidin, a fluorophore, a nucleic acid, an isotope, or other label.

One or more screening peptides are optionally used to determine the presence or absence of antibodies that specifically bind one or more of the screening peptides in a biological sample. A positive result is discerned when an antibody is found in the biological sample that binds to a specific peptide. By contacting a library of peptides to a biological sample, or portions thereof, the epitope regions of any anti-PA antibodies present in the sample are readily discernable. The presence or absence of an antibody to one or more predefined regions encompassed by the peptide(s) is used to determine protection to B. anthracis in the subject from which the biological sample is derived.

The presence or absence of antibodies to one or more predefined regions of mature PA indicates that a subject possesses an immunity to B. anthracis or lacks sufficient immunity to B. anthracis infection. The presence of an antibody to a predefined region that positively correlates to protection indicates protection from B. anthracis infection. The presence of an antibody to a predefined region that negatively correlates with protection indicates a susceptibility or lack of protection to B. anthracis. An illustrative predefined region that negatively correlates to protection are peptides 35, 28, or an immunogenic portion thereof. Optionally, the presence of antibodies to one or more positively correlating predetermined regions and the absence of antibodies to one or more negatively correlating predetermined regions indicates protection to complications from subsequent infection by B. anthracis.

Figure 6:
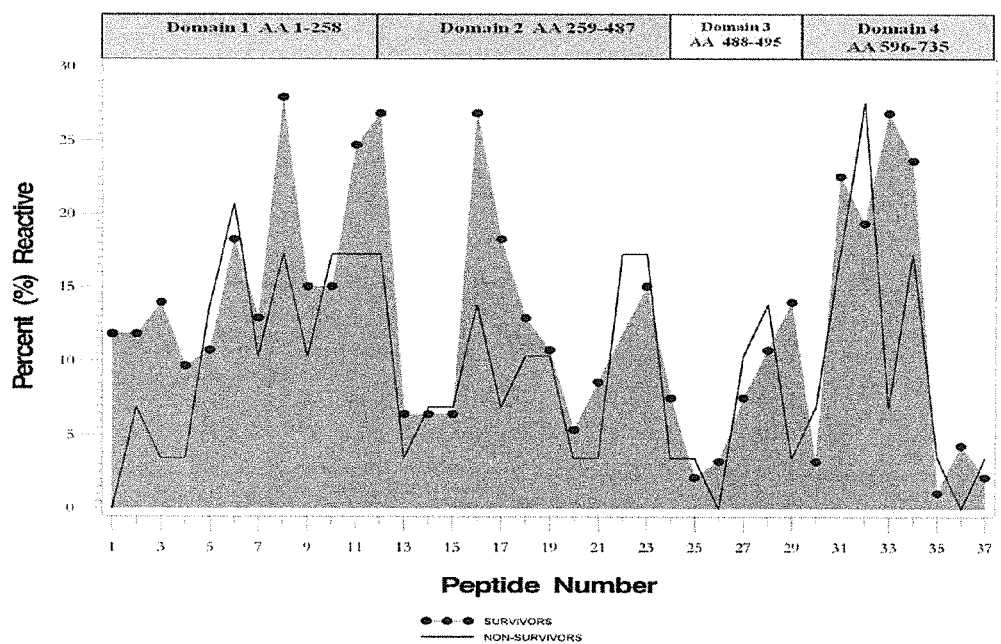
FIG. 6 represents the frequency of antibody responses to protective antigen synthetic peptides in macaques' serum at 30 wk. post vaccination with 3 intra-muscular AVA injections (0, 4, 26 weeks) where animals were subsequently challenged with 220-400 LD50 of aerosolized *B. anthracis* Ames spores and sera were grouped by survivors (n=78) and non-survivors (n=19)
Figure 7:
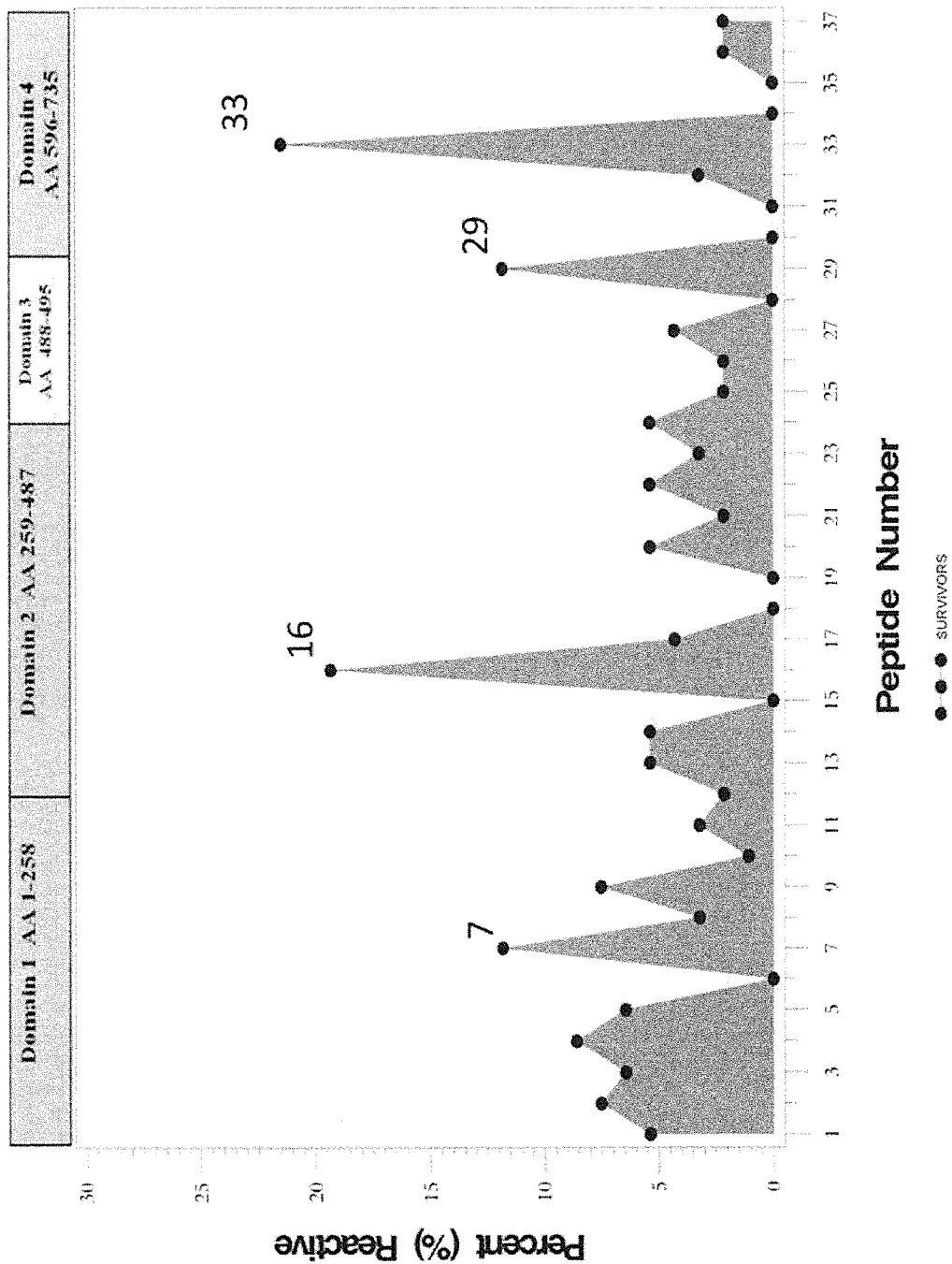
FIG. 7 represents the frequency of immune response to protective antigen synthetic peptides in macaques at 30 wk. post vaccination with 3 intra-muscular AVA injections (0, 4, 26 weeks) using a maximum OD value from non-survivor macaques as a reactivity threshold.

It was surprisingly discovered that the presence of antibodies to peptide 35, 28, or an immunogenic portion thereof negatively correlates to protection. As is observed in FIGS. 6 and 7, this region of PA is poorly immunogenic such that it was not expected that this region would show any correlation with protection at all either positive or negative. However, the statistical analyses clearly demonstrate that the presence of antibodies the specifically bind this region of mature PA indicates a susceptibility to complications from infection by B. anthracis.

Optionally, a plurality of predefined regions are used to determine the correlate of infection that together provide significantly improved predictability of protection when used in combination than any predefined region alone, and result in far superior prediction of protection relative to general measurements of IgG to PA. Such a plurality of predefined regions includes

TABLE 1

Groups of predefined regions of PA that illustrate an improved prediction of protection to subsequent B. anthracis infection where simple measurements of ED50 (dilution of serum effecting 50% neutralization of lethal toxin and measured by toxin neutralization assay (TNA)) has an ROC of 0.7652.

| Group of Peptides | Receiver Operating Characteristic |
|---|---|
| 3, 28, 29, 33, 35 | 0.8570 |
| 3, 16, 21, 28, 33 | 0.8462 |
| 28, 29, 33, 35 | 0.8428 |
| 28, 35 | 0.8117 |
| 3, 16, 21, 29, 33 | 0.8003 |
| 7, 16, 29, 33 | 0.7800 |
| 29, 33 | 0.7740 |
| 29, 35 | 0.7733 |

Optionally, peptides to one or more of these groups are used as screening peptides. Optionally, a screening assay includes only one or more of peptide 3, 7, 16, 21, 28, 29, 33, and 35. The identification of particular groups of peptides that demonstrate as a group or individually superior correlation of protection relative to complete anti-PA IgG measurements allows for much greater simplicity in a screening assay. For example, a screening assay need not include peptide regions that cover the full length of PA, but instead are specifically targeted to the defined predetermined regions such as those described herein.

Optionally, a screening peptide includes a single epitope. Optionally, the number of single epitope screening peptides included in an assay is no more than 2, 3, 4, 5, or 6. Optionally, the number of single epitope containing screening peptides is 2, 3, 4, or 5.

In some embodiments, a vaccine is administered to a subject prior to, simultaneously with, or subsequent to obtaining a biological sample from the subject. Optionally, a vaccine is administered and then an onset time elapses prior to obtaining a biological sample from the subject. An onset time is a time that is generally considered by those of skill in the art to be sufficient for a subject to produce an antibody to a portion of an immunogen, such as an immunogen of the prior art. Optionally, an onset time is 1, 2, 3, 4, 5, 6, or more days. Optionally, an onset time is 1, 2, 3, 4, 5, 6, or more weeks. An onset time is optionally any time between 1 day and 60 days, or any fraction or specific time period therebetween.

A process optionally includes a first administration of a vaccine, a first onset time, and then subsequently obtaining a first biological sample. A process optionally also includes determining whether a second administration is required by the presence or absence of an antibody to a peptide in the biological sample. Optionally, a second administration is performed followed by a second onset time and obtaining a second biological sample for screening for the presence or absence of antibodies to one or more peptides. This iterative process optionally continues until a subject demonstrates acquired immunity or a physician determines that development of immunity is not possible in the subject. As such, a third, fourth, fifth, or additional administration is envisioned under the invention. Similarly, a third, fourth, fifth, or subsequent onset time is envisioned under the invention.

Also provided are vaccines that when administered to a subject will elicit an immune response. The term "immune response" refers to a kinetic or magnitude variation of one or more elements of a subject's immune system. An immune response is optionally the production of antibodies that specifically recognize and interact with the vaccine. Non-limiting examples of immune responses include B-cell responses, calcium mobilization, calcium influx, or other changes in intracellular calcium concentrations in any cellular compartment illustratively including the cytoplasm; nitric oxide production or release; phagocytosis; immunoglobulin uptake; production of immunoglobulin; alteration of protein phosphorylation; conversion of immune complexes; alteration of serum immunoglobulin levels; modulating the activity of spleen tyrosine kinase (Syk), B-cell linker (BLNK), Burton's tyrosine kinase (Btk), Kit, Lck, Zap-70, Src, Stat1, SHP-2, phosphatidyl inositol 3-kinase (PI3K), phosphoinositol 5-phosphatase, other kinases or phosphatases known in the art, phospholipase D, phospholipase C, sphingosine kinase; secretion of IL-1β, IL-6, IL-10, IL-2, IL-4, IFN-γ, Bcl10, TCR, TLR, or other cytokines, chemokines, or signaling molecules; interferon signaling; alteration of expression of interferon response gene(s) (IRG); antibody production illustratively IgE or IgG production; alteration of the expression of any gene that encodes for a protein; alteration of expression or activity of My4+/LeuM3− molecule; protection from challenge after exposure to infectious organism; alteration in nitrite levels; B-cell responses in various immune compartments; lymphoma cell responses; natural killer cell responses; monocyte responses; macrophage responses; platelet responses; dendritic cell responses; any immune cell response; Th1 and Th2 cytokine responses in various immune compartments; immune cell maturation; activation or inhibition of an intracellular signaling pathway such as the NF-kappa B signaling pathway; apoptosis; alteration in allotype or isotype antibody levels; in vitro recognition of antigen; survival; other response known in the art; or combinations thereof.

It is appreciated that the peptides of the invention may be representative vaccines operable under the invention with the exception of a peptide encoding an immunogenic portion of peptide 35 or peptide 28. As such, any peptide vaccine described herein is suitable in the inventive processes for determining whether a subject has acquired immunity or is at risk for subsequent infection by B. anthracis. The terms "polypeptide," "peptide," are used interchangeably herein and are illustratively a chain of two or more amino acid residues. In some embodiments, a peptide suitable for use in the instant invention is the amino acid sequence for PA protein, fragments thereof, or analogues thereof used alone or combined with other peptides or otherwise immunogenic sequence(s) or therapeutics. A peptide is optionally an immunogen. It is appreciated that an immunogen is any molecule used to vaccinate an organism. As such, an immunogen is optionally a peptide, a nucleic acid, or combinations thereof.

A vaccine optionally includes one or more predefined regions of PA, or an analogue thereof. In some embodiments, a vaccine is a nucleic acid sequence that encodes a predefined region of PA such that when the nucleic acid sequence is administered to a subject, the predefined peptide sequence is expressed by the subject to act as an immunogen for the generation of antibodies to the predefined sequence.

Optionally, inventive peptide sequences representing predefined regions of PA useful as vaccines are: AA41-70 of mature PA; 121-150 of mature PA; the calcium ion chelating residues in the $1\alpha_1$ and $1\beta_{13}$ strands, (AA181-210); $1\beta_{13}$, $1\alpha_2$, $1\beta_{14}$ (AA201-230); $1\alpha_3$ and $1\alpha_4$ (AA 221-250); and $1\alpha_4$ and $2\beta_1$ (AA241-270) regions in domain 1; the chymotrypsin sensitive loop $2\beta_2$-$2\beta_3$ (AA 301-330); $2\beta_3$ and $2\alpha_1$ (AA 321-350); $2\alpha_1$, $2\beta_4$ and $2\beta_5$ (AA341-370); 2136 and 2137 (AA361-390); $2\beta_{10}$, $2\beta_{11}$, $2\alpha_2$ and $2\beta_{12}$ (AA421-450); AA 541-570 of mature PA; $2\beta_{13}$ in domain 2, $3\alpha_3$, $3\alpha_4$ (AA 561-590); $3\beta_7$, $3\beta_8$ (AA581-610) in domain 3 and partially in domain 4 of PA; and AA641-670 in domain 4 of PA, analogues thereof, immunogenic fragments thereof; or combinations thereof. When a peptide is used as a vaccine, analogues of a peptide are operable as an immunogen. An analogue of an immunogen peptide will elicit the production of antibodies with sufficient affinity to the wild type PA sequence to be used as biological antibodies to the wild type sequence.

Optionally, peptides used either as an immunogen or as a screening peptide are chemically synthesized or recombinant, and are obtained by methods known in the art. Illustratively, a nucleotide sequence may be cloned into a plasmid which is transfected into *E. coli* and expressed. The nucleotide sequence encoding immature PA is illustrated as SEQ ID NO: 2.

```
                                          (SEQ ID NO: 2)
AATTTCAATA TAATATAAAT TTAATTTTAT ACAAAAAGGA

GAACGTATAT GAAAAAACGA AAAGTGTTAA TACCATTAAT

GGCATTGTCT ACGATATTAG TTTCAAGCAC AGGTAATTTA

GAGGTGATTC AGGCAGAAGT TAAACAGGAG AACCGGTTAT

TAAATGAATC AGAATACAGT TCCCAGGGGT TACTAGGATA

CTATTTTAGT GATTTGAATT TTCAAGCACC CATGGTGGTT

ACTTCTTCTA CTACAGGGGA TTTATCTATT CCTAGTTCTG

AGTTAGAAAA TATTCCATCG GAAAACCAAT ATTTTCAATC

TGCTATTTGG TCAGGATTTA TCAAAGTTAA GAAGAGTGAT

GAATATACAT TTGCTACTTC CGCTGATAAT CATGTAACAA

TGTGGGTAGA TGACCAAGAA GTGATTAATA AAGCTTCTAA

TTCTAACAAA ATCAGATTAG AAAAAGGAAG ATTATATCAA

ATAAAAATTC AATATCAACG AGAAAATCCT ACTGAAAAAG

GATTGGATTT CAAGTTGTAC TGGACCGATT CTCAAAATAA

AAAAGAAGTG ATTTCTAGTG ATAACTTACA ATTGCCAGAA

TTAAAACAAA AATCTTCGAA CTCAAGAAAA AAGCGAAGTA

CAAGTGCTGG ACCTACGGTT CCAGACCGTG ACAATGATGG

AATCCCTGAT TCATTAGAGG TAGAAGGATA TACGGTTGAT

GTCAAAAATA AAAGAACTTT TCTTTCACCA TGGATTTCTA

ATATTCATGA AAAGAAAGGA TTAACCAAAT ATAAATCATC

TCCTGAAAAA TGGAGCACGG CTTCTGATCC GTACAGTGAT

TTCGAAAAGG TTACAGGACG GATTGATAAG AATGTATCAC

CAGAGGCAAG ACACCCCCTT GTGGCAGCTT ATCCGATTGT

ACATGTAGAT ATGGAGAATA TTATTCTCTC

AAAAAATGAGGATCAATCCA CACAGAATAC TGATAGTCAA

ACGAGAACAA TAAGTAAAAA TACTTCTACA AGTAGGACAC

ATACTAGTGA AGTACATGGA AATGCAGAAG TGCATGCGTC

GTTCTTTGAT ATTGGTGGGA GTGTATCTGC AGGATTTAGT

AATTCGAATT CAAGTACGGT CGCAATTGAT CATTCACTAT

CTCTAGCAGG GGAAAGAACT TGGGCTGAAA CAATGGGTTT

AAATACCGCT GATACAGCAA GATTAAATGC CAATATTAGA

TATGTAAATA CTGGGACGGC TCCAATCTAC AACGTGTTAC

CAACGACTTC GTTAGTGTTA GGAAAAAATC AAACACTCGC

GACAATTAAA GCTAAGGAAA ACCAATTAAG TCAAATACTT

GCACCTAATA ATTATTATCC TTCTAAAAAC TTGGCGCCAA

TCGCATTAAA TGCACAAGAC GATTTCAGTT CTACTCCAAT

TACAATGAAT TACAATCAAT TTCTTGAGTT AGAAAAAACG

AAACAATTAA GATTAGATAC GGATCAAGTA TATGGGAATA

TAGCAACATA CAATTTTGAA AATGGAAGAG TGAGGGTGGA

TACAGGCTCG AACTGGAGTG AAGTGTTACC GCAAATTCAA

GAAACAACTG CACGTATCAT TTTTAATGGA AAAGATTTAA

ATCTGGTAGA AAGGCGGATA GCGGCGGTTA ATCCTAGTGA

TCCATTAGAA ACGACTAAAC CGGATATGAC ATTAAAAGAA

GCCCTTAAAA TAGCATTTGG ATTTAACGAA TCGAATGGAA

ACTTACAATA TCAAGGGAAA GACATAACCG AATTTGATTT

TAATTTCGAT CAACAAACAT CTCAAAATAT CAAGAATCAG

TTAGCGGAAT TAAACGTAAC TAACATATAT ACTGTATTAG

ATAAAATCAA ATTAAATGCA AAAATGAATA TTTTAATAAG

AGATAAACGT TTTCATTATG ATAGAAATAA CATAGCAGTT

GGGGCGGATG AGTCAGTAGT TAAGGAGGCT CATAGAGAAG

TAATTAATTC GTCAACAGAG GGATTATTGT TAAATATTGA

TAAGGATATA AGAAAAATAT TATCAGGTTA TATTGTAGAA

ATTGAAGATA CTGAAGGGCT TAAAGAAGTT ATAAATGACA

GATATGATAT GTTGAATATT TCTAGTTTAC GGCAAGATGG

AAAAACATTT ATAGATTTTA AAAAATATAA TGATAAATTA
```

```
                            -continued
CCGTTATATA   TAAGTAATCC   CAATTATAAG   GTAAATGTAT

ATGCTGTTAC   TAAAGAAAAC   ACTATTATTA   ATCCTAGTGA

GAATGGGGAT   ACTAGTACCA   ACGGGATCAA   GAAAATTTTA

ATCTTTTCTA   AAAAAGGCTA   TGAGATAGGA   TAAGGTAATT

CTAGGTGATT   TTTAAATTA
```

It is appreciated that any portion of SEQ ID NO: 2, or a variant thereof, that will encode a peptide of the invention is operable herein for the production of a peptide or for use as a vaccine itself or as a screening peptide. An inventive nucleic acid sequence that encodes a peptide of SEQ ID NO: 1, SEQ ID NO: 3, other peptide sequences herein, fragments thereof, or analogues thereof is encompassed in the invention. Similarly, variants of SEQ ID NO: 2, or fragments thereof are operable to encode a peptide of the invention. The genetic code is a degenerate code whereby specific nucleic acid sequences encode for particular amino acids, yet in most cases more than one codon (three nucleotide sequence) will encode for the same amino acid. It is therefore appreciated that a variant of SEQ ID NO: 2, SEQ ID NO: 1, or a fragment thereof, that encodes a polypeptide under the invention is a nucleic acid sequence of the invention. It is well within the level of those of skill in the art to determine a nucleic acid sequence that will encode the inventive peptide immunogens.

A vaccine according to the invention includes a predefined sequence of PA or an analogue thereof. Amino acids present in a vaccine or peptide include the common amino acids alanine, cysteine, aspartic acid, glutamic acid, phenylalanine, glycine, histidine, isoleucine, lysine, leucine, methionine, asparagine, proline, glutamine, arginine, serine, threonine, valine, tryptophan, and tyrosine as well as less common naturally occurring amino acids, modified amino acids or synthetic compounds, such as alpha-asparagine, 2-aminobutanoic acid or 2-aminobutyric acid, 4-aminobutyric acid, 2-aminocapric acid (2-aminodecanoic acid), 6-aminocaproic acid, alpha-glutamine, 2-aminoheptanoic acid, 6-aminohexanoic acid, alpha-aminoisobutyric acid (2-aminoalanine), 3-aminoisobutyric acid, beta-alanine, allo-hydroxylysine, allo-isoleucine, 4-amino-7-methylheptanoic acid, 4-amino-5-phenylpentanoic acid, 2-aminopimelic acid, gamma-amino-beta-hydroxybenzenepentanoic acid, 2-aminosuberic acid, 2-carboxyazetidine, beta-alanine, beta-aspartic acid, biphenylalanine, 3,6-diaminohexanoic acid, butanoic acid, cyclobutyl alanine, cyclohexylalanine, cyclohexylglycine, N5-aminocarbonylornithine, cyclopentyl alanine, cyclopropyl alanine, 3-sulfoalanine, 2,4-diaminobutanoic acid, diaminopropionic acid, 2,4-diaminobutyric acid, diphenyl alanine, N,N-dimethylglycine, diaminopimelic acid, 2,3-diaminopropanoic acid, S-ethylthiocysteine, N-ethylasparagine, N-ethylglycine, 4-aza-phenylalanine, 4-fluoro-phenylalanine, gamma-glutamic acid, gamma-carboxyglutamic acid, hydroxyacetic acid, pyroglutamic acid, homoarginine, homocysteic acid, homocysteine, homohistidine, 2-hydroxyisovaleric acid, homophenylalanine, homoleucine, homoproline, homoserine, homoserine, 2-hydroxypentanoic acid, 5-hydroxylysine, 4-hydroxyproline, 2-carboxyoctahydroindole, 3-carboxylsoquinoline, isovaline, 2-hydroxypropanoic acid (lactic acid), mercaptoacetic acid, mercaptobutanoic acid, sarcosine, 4-methyl-3-hydroxyproline, mercaptopropanoic acid, norleucine, nipecotic acid, nortyrosine, norvaline, omega-amino acid, ornithine, penicillamine (3-mercaptovaline), 2-phenylglycine, 2-carboxypiperidine, sarcosine (N-methylglycine), 2-amino-3-(4-sulfophenyl)propionic acid, 1-amino-1-carboxycyclopentane, 3-thienylalanine, epsilon-N-trimethyllysine, 3-thiazolylalanine, thiazolidine 4-carboxylic acid, alpha-amino-2,4-dioxopyrimidinepropanoic acid, and 2-naphthylalanine. A peptide optionally has between 2 and about 60 amino acids.

A peptide is obtained by any of various methods known in the art illustratively including isolation from a cell or organism, chemical synthesis, expression of a nucleic acid sequence, and partial hydrolysis of proteins. Chemical methods of peptide synthesis are known in the art and include solid phase peptide synthesis and solution phase peptide synthesis or by the method of Hackeng, T M, et al., *Proc Natl Acad Sci USA,* 1997; 94 (15):7845-50 or those reviewed by Miranda, L P, *Peptide Science,* 2000, 55:217-26 and Kochendoerfer G G, *Curr Opin Drug Discov Devel.* 2001; 4 (2):205-14. In some embodiments, the polypeptide sequences are chemically synthesized by Fmoc synthesis.

The present invention encompasses an isolated peptide derived from mature or immature PA of *B. anthracis.* An inventive PA immunogen has the sequence represented by a fragment of SEQ ID NO: 1 wherein the fragment includes at least a portion of: AA121-150 of mature PA; AA41-70 of mature PA; the calcium ion chelating residues in the $1\alpha_1$ and $1\beta_{13}$ strands, (AA181-210); $1\beta_{13}$, $1\alpha_2$, $1\beta_{14}$ (AA201-230); $1\alpha_3$ and $1\alpha_4$ (AA 221-250); and $1\alpha_4$ and $2\beta_1$ (AA241-270) regions in domain 1; the chymotrypsin sensitive loop $2\beta_2$-$2\beta_3$ (AA 301-330); $2\beta_3$ and $2\alpha_1$ (AA 321-350); $2\alpha_1$, $2\beta_4$ and $2\beta_5$ (AA341-370); $2\beta_6$ and $2\beta_7$ (AA361-390); $2\beta_{10}$, $2\beta_{11}$, $2\alpha_2$ and $2\beta_{12}$ (AA421-450); AA541-570 of mature PA; $2\beta_{13}$ in domain 2, $3\alpha_3$, $3\alpha_4$ (AA 561-590); $3\beta_7$, $3\beta_8$ (AA581-610) in domain 3 and partially in domain 4 of PA; AA661-690 of mature PA; immunogenic portions thereof; or combinations thereof. A peptide immunogen is optionally recombinant. However, it is also envisioned that naturally occurring PA immunogen may be isolated from at least a portion of the cellular and other sample material for which the wild-type sequence is normally found. Methods for purification of protein from organism derived samples are known and are within the level of skill in the art, illustratively affinity chromatography.

To ease purification or screening procedures, the expressed polypeptides optionally include a tag sequence. Illustrative examples of tags suitable for use in the instant invention include poly-histidine, CBP, CYD (covalent yet dissociable NorpD peptide), strep-2, FLAG, HPC or heavy chain of protein C peptide tag, biotin, avidin, or GST and MBP protein fusion tag systems. It is appreciated that other tag systems are similarly operable. In some embodiments, recombinant peptides are expressed in *E. coli* and purified using an affinity tag system followed by enzymatic cleavage of the tag such as by incorporating a factor Xa, thrombin, or other enzyme cleavage site in the expressed polypeptide. Methods of tag cleavage are known in the art and any effective method is appreciated to be suitable for use in the instant invention.

It is recognized that numerous analogues of a peptide are within the scope of the present invention including amino acid substitutions, alterations, modifications, or other amino acid changes that increase, decrease, or do not alter the function or immunogenic propensity of the inventive immunogen. Several post-translational modifications are similarly envisioned as within the scope of the present invention illustratively including incorporation of a non-naturally occurring amino acid(s), phosphorylation, glycosylation, sulfation, and addition of pendent groups such as biotynlation, fluorophores, lumiphores, radioactive groups, antigens, or other molecules.

It is appreciated that the inventive peptides of the present invention are phosphorylated or unphosphorylated. Optionally, an inventive peptide is disulfide bonded. Disulfide bonds can be to amino acid residues within the sequence or to a second polypeptide or molecule.

Modifications and changes can be made in the structure of the inventive peptides that are the subject of the application and still obtain a molecule having similar or improved characteristics as the wild-type sequence (e.g., a conservative amino acid substitution). For example, certain amino acids can be substituted for other amino acids in a sequence without appreciable loss of immunogenic activity. Because it is the interactive capacity and nature of a polypeptide that defines that polypeptide's biological functional activity, certain amino acid sequence substitutions can be made in a polypeptide sequence and nevertheless obtain a polypeptide with like or improved properties. Optionally, a polypeptide is used that has less or more immunogenic activity compared to the wild-type sequence.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In making such changes, the substitution of amino acids whose hydropathic indices are within ±2 is optional, those within ±1 are optional, and those within ±0.5 are similarly optional.

Substitution of like amino acids can also be made on the basis of hydrophilicity, particularly, where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is optional, those within ±1 are optional, and those within ±0.5 are optional.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

It is appreciated that amino acids are optionally L- or D-isomers. An inventive polypeptide optionally includes mixtures of L- and D-isomers.

Peptide expression is illustratively accomplished from transcription of a nucleic acid sequence encoding a peptide of the invention, and translation of RNA transcribed from nucleic acid sequence, modifications thereof, or fragments thereof. Protein expression is optionally performed in a cell based system such as in *E. coli*, Hela cells, or Chinese hamster ovary cells. It is appreciated that cell-free expression systems are similarly operable.

It is recognized that numerous analogues of a peptide are within the scope of the present invention including amino acid substitutions, alterations, modifications, or other amino acid changes that increase, decrease, or do not alter the function or the ability of PA immunogen to generate antibodies that will interact with a wild-type PA protein sequence. It is appreciated that an analogue includes one or more amino acid insertions, deletions, substitutions, or modifications. An analogue of SEQ ID NO: 1, SEQ ID NO: 3, or any other amino acid sequence taught herein is sufficiently immunogenic in a host to produce an antibody that will specifically bind to at least a portion of wild-type PA. One of ordinary skill in the art understands how to produce antibodies by standard techniques and screen the resulting monoclonal or polyclonal antibodies for their ability to interact with an epitope sequence. Such methods are illustratively taught by Monoclonal Antibodies: Methods and Protocols, Albitar, M, ed., Humana Press, 2010 (ISBN 1617376469); and Antibodies: A Laboratory Manual, Harlos, E, and Lane, D. eds., Cold Spring Harbor Laboratory Press, 1988 (ISBN-10: 0879693142).

Further aspects of the present disclosure concern the purification, and in particular embodiments, the substantial purification, of a peptide. The term "purified" or "isolated" peptide as used herein, is intended to refer to a composition, isolatable from other components, wherein the PA immunogen is purified to any degree relative to its naturally-obtainable state. A purified peptide, therefore, also refers to a peptide free from the environment in which it may naturally occur.

Generally, "purified" or "isolated" will refer to a peptide composition that has been subjected to fractionation to remove various other components, and which composition substantially retains its expressed biological activity. Where the term "substantially" purified is used, this designation will refer to a composition in which the protein or peptide forms the major component of the composition, such as constituting about 50% or more of the proteins in the composition.

Various methods for quantifying the degree of purification of the peptide known to those of skill in the art in light of the present disclosure as based on knowledge in the art. These include, for example, determining the specific activity of an active fraction, or assessing the number of peptides within a fraction by SDS/PAGE analysis. An illustrative method for assessing the purity of a fraction is to calculate the specific activity of the fraction, to compare it to the specific activity of the initial extract, and to thus calculate the degree of purity, herein assessed by a "-fold purification number". The actual units used to represent the amount of activity will, of course, be dependent upon the particular assay technique chosen to follow the purification and whether or not the expressed protein or peptide exhibits a detectable activity.

Various techniques suitable for use in peptide purification will be well known to those of skill in the art. These include, for example, precipitation with ammonium sulphate, polyethylene glycol, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

Additional methods of peptide isolation illustratively include column chromatography, affinity chromatography, gel electrophoresis, filtration, or other methods known in the art. In some embodiments, an immunogen is expressed with a tag operable for affinity purification. An illustrative tag is a 6×His tag. A 6×His tagged inventive peptide immunogen is illustratively purified by Ni-NTA column chromatography or using an anti-6×His tag antibody fused to a solid support. (Geneway Biotech, San Diego, Calif.) Other tags and purification systems are similarly operable.

It is appreciated that an inventive peptide is optionally not tagged. In this embodiment and other embodiments purification is optionally achieved by methods known in the art illustratively including ion-exchange chromatography, affinity chromatography using antibodies directed to the peptide sequence of interest, precipitation with salt such as ammonium sulfate, streptomycin sulfate, or protamine sulfate, reverse phase chromatography, size exclusion chromatography such as gel exclusion chromatography, HPLC, immobilized metal chelate chromatography, or other methods known in the art. One of skill in the art may select the most appropriate isolation and purification techniques without departing from the scope of this invention.

There is no general requirement that the peptide always be provided in its most purified state. It is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater-fold purification than the same technique utilizing a low pressure chromatography system. Methods exhibiting a lower degree of relative purification may have advantages in total recovery of protein product, or in maintaining the activity of an expressed protein.

It is known that the migration of a peptide can vary, sometimes significantly, with different conditions of SDS/PAGE (Capaldi et al., *Biochem. Biophys. Res. Comm.*, 76:425, 1977). It will, therefore, be appreciated that under differing electrophoresis conditions, the apparent molecular weights of purified or partially purified expression products may vary.

PA immunogens or screening peptides of this invention may optionally be characterized by measurements including, without limitation, western blot, macromolecular mass determinations by biophysical determinations, SDS-PAGE/staining, HPLC and the like, antibody recognition assays, cell viability assays, apoptosis assays, and assays to infer immune protection or immune pathology by adoptive transfer of cells, proteins or antibodies.

Also provided are isolated nucleic acids encoding the desired peptide sequence analogues thereof, or fragments thereof. These nucleic acids can be used to produce the peptides of this invention or as nucleic acid vaccines, wherein the peptides of this invention are produced in a subject.

The term "nucleotide" is intended to mean a base-sugar-phosphate combination either natural or synthetic, linear, circular and sequential arrays of nucleotides and nucleosides, e.g. cDNA, genomic DNA, mRNA, and RNA, oligonucleotides, oligonucleosides, and derivatives thereof. Included in this definition are modified nucleotides which include additions to the sugar-phosphate groups as well as to the bases.

The term "nucleic acid" or "polynucleotide" refers to multiple nucleotides attached in the form of a single or double stranded polynucleotide that can be natural, or derived synthetically, enzymatically, and by cloning methods. The term "oligonucleotide" refers to a polynucleotide of less than 200 nucleotides. The terms "nucleic acid" and "oligonucleotide" may be used interchangeably in this application.

A nucleic acid as used herein refers to single- or double-stranded molecules that may be DNA, including of the nucleotide bases A, T, C and G, or RNA, comprised of the bases A, U (substitutes for T), C, and G. The nucleic acid may represent a coding strand or its complement. Nucleic acids may be identical in sequence to the sequence naturally occurring, illustratively SEQ ID NO: 2 or a fragment thereof, or may include alternative codons that encode the same amino acid as that found in the naturally occurring sequence. Furthermore, nucleic acids may include codons that represent conservative substitutions of amino acids as are well known in the art.

The nucleic acid encoding the peptide of this invention can be part of a recombinant nucleic acid construct comprising any combination of restriction sites and/or functional elements as are well known in the art that facilitate molecular cloning and other recombinant DNA manipulations. Thus, the present invention further provides a recombinant nucleic acid construct comprising a nucleic acid encoding a peptide of this invention.

The present invention also provides a vector with a nucleic acid sequence encoding an inventive PA immunogen or screening peptide sequence therein. Illustrative vectors include a plasmid, cosmid, cationic lipids, non-liposomal cationic vectors, cationic cyclodextrin, viruses with RNA or DNA genetic material, polyethylenimines, histidylated polylysine, or other vector system known in the art. A vector is optionally a plasmid. A suitable vector optionally possesses cell type specific expression or other regulatory sequences or sequences operable to stimulate or inhibit gene or protein expression. A vector illustratively contains a selection marker such as an antibiotic resistance gene.

The inventive nucleic acid sequence is optionally isolated from the cellular materials with which it is naturally associated. As used herein, the term "isolated nucleic acid" means a nucleic acid separated or substantially free from at least some of the other components of the naturally occurring organism, for example, the cell structural components commonly found associated with nucleic acids in a cellular environment and/or other nucleic acids. The isolation of nucleic acids is optionally accomplished by techniques such as cell lysis followed by phenol plus chloroform extraction, followed by ethanol precipitation of the nucleic acids. The nucleic acids of this invention can be isolated from cells according to methods well known in the art for isolating nucleic acids. Alternatively, the nucleic acids of the present invention can be synthesized according to standard protocols well described in the literature for synthesizing nucleic acids. Modifications to the nucleic acids of the invention are also contemplated, provided that the essential structure and function of the peptide encoded by the nucleic acid are maintained.

Numerous methods are known in the art for the synthesis and production of nucleic acid sequences illustratively including cloning and expression in cells such as E. coli, insect cells such as Sf9 cells, yeast, and mammalian cell types such as Hela cells, Chinese hamster ovary cells, or other cells systems known in the art as amendable to transfection and nucleic acid and/or protein expression. Methods of nucleic acid isolation are similarly recognized in the art. Illustratively, plasmid DNA amplified in E. coli is cleaved by suitable restriction enzymes such as NdeI and XhoI to linearize PA DNA. The PA DNA is subsequently isolated following gel electrophoresis using a S.N.A.P.™ UV-Free Gel Purification Kit (Invitrogen, Carlsbad, Calif.) as per the manufacturer's instructions.

Numerous agents are amenable to facilitate cell transfection illustratively including synthetic or natural transfection agents such as LIPOFECTIN, baculovirus, naked plasmid or other DNA, or other systems known in the art.

The nucleic acid sequences of the invention may be isolated or amplified by conventional uses of polymerase chain reaction or cloning techniques such as those described in conventional texts. For example, the nucleic acid sequences of this invention may be prepared or isolated from DNA using DNA primers and PCR techniques. Alternatively, the inventive PA nucleic acid sequence may be obtained from gene banks derived from *B. anthracis* whole genomic DNA. These sequences, fragments thereof, modifications thereto and the full-length sequences may be constructed recombinantly using conventional genetic engineering or chemical synthesis techniques or PCR, and the like.

Also provided is a host cell transformed with an appropriate vector or with the inventive PA peptide sequence. Illustrative host cells include *E. coli* or Sf9 cells. Optionally, cell transfection is achieved by electroporation.

Recombinant or non-recombinant proteinase peptides or recombinant or non-recombinant proteinase inhibitor peptides or other non-peptide proteinase inhibitors can also be used in the present invention. Proteinase inhibitors are optionally modified to resist degradation, for example degradation by digestive enzymes and conditions. Techniques for the expression and purification of recombinant proteins are known in the art (see Sambrook Eds., Molecular Cloning: A Laboratory Manual $3^{rd}$ ed. (Cold Spring Harbor, N.Y. 2001).

Some embodiments of the present invention are compositions containing a nucleic acid sequence that can be expressed as a peptide according to the invention. The engineering of DNA segment(s) for expression in a prokaryotic or eukaryotic system may be performed by techniques generally known to those of skill in recombinant expression. It is believed that virtually any expression system may be employed in the expression of the claimed nucleic acid and amino acid sequences.

As used herein, the terms "engineered" and "recombinant" cells are synonymous with "host" cells and are intended to refer to a cell into which an exogenous DNA segment or gene, such as a cDNA or gene has been introduced. Therefore, engineered cells are distinguishable from naturally occurring cells which do not contain a recombinantly introduced exogenous DNA segment or gene. A host cell is optionally a naturally occurring cell that is transformed with an exogenous DNA segment or gene or a cell that is not modified. Engineered cells are cells having a gene or genes introduced through the hand of man. Recombinant cells include those having an introduced cDNA or genomic DNA, and also include genes positioned adjacent to a promoter not naturally associated with the particular introduced gene.

To express a recombinant peptide in accordance with the present invention one optionally prepares an expression vector that comprises a nucleic acid under the control of one or more promoters. To bring a coding sequence "under the control of" a promoter, one positions the 5' end of the translational initiation site of the reading frame generally between about 1 and 50 nucleotides "downstream" of (i.e., 3' of) the chosen promoter. The "upstream" promoter stimulates transcription of the inserted DNA and promotes expression of the encoded recombinant protein. This is the meaning of "recombinant expression" in the context used here.

Many standard techniques are available to construct expression vectors containing the appropriate nucleic acids and transcriptional/translational control sequences in order to achieve peptide expression in a variety of host-expression systems. Cell types available for expression include, but are not limited to, bacteria, such as *E. coli* and *B. subtilis* transformed with recombinant phage DNA, plasmid DNA or cosmid DNA expression vectors.

Certain examples of prokaryotic hosts are *E. coli* strain RR1, *E. coli* LE392, *E. coli* B, *E. coli* .chi. 1776 (ATCC No. 31537) as well as *E. coli* W3110 (F-, lambda-, prototrophic, ATCC No. 273325); bacilli such as *B. subtilis*; and other enterobacteriaceae such as *Salmonella typhimurium, Serratia marcescens*, and various *Pseudomonas* species.

In general, plasmid vectors containing replicon and control sequences that are derived from species compatible with the host cell are used in connection with these hosts. The vector ordinarily carries a replication site, as well as marking sequences that are capable of providing phenotypic selection in transformed cells. For example, *E. coli* is often transformed using pBR322, a plasmid derived from an *E. coli* species. Plasmid pBR322 contains genes for ampicillin and tetracycline resistance and thus provides easy means for identifying transformed cells. The pBR322 plasmid, or other microbial plasmid or phage must also contain, or be modified to contain, promoters that can be used by the microbial organism for expression of its own proteins.

In addition, phage vectors containing replicon and control sequences that are compatible with the host microorganism can be used as transforming vectors in connection with these hosts. For example, the phage lambda may be utilized in making a recombinant phage vector that can be used to transform host cells, such as *E. coli* LE392.

Further useful vectors include pIN vectors and pGEX vectors, for use in generating glutathione S-transferase (GST) soluble fusion proteins for later purification and separation or cleavage. Other suitable fusion proteins are those with β-galactosidase, ubiquitin, or the like.

Promoters that are most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

For expression in *Saccharomyces*, the plasmid YRp7, for example, is commonly used. This plasmid contains the trp1 gene, which provides a selection marker for a mutant strain of yeast lacking the ability to grow in tryptophan, for example ATCC No. 44076 or PEP4-1. The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other suitable promoters, which have the additional advantage of transcription controlled by growth conditions, include the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization.

In addition to microorganisms, cultures of cells derived from multicellular organisms may also be used as hosts. In principle, any such cell culture is operable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing one or more coding sequences.

In a useful insect system, *Autographica californica* nuclear polyhedrosis virus (AcNPV) is used as a vector to express foreign genes. The virus grows in *Spodoptera frugiperda* cells. The isolated nucleic acid coding sequences are cloned into non-essential regions (for example the polyhedron gene) of the virus and placed under control of an AcNPV promoter (for example, the polyhedron promoter). Successful insertion of the coding sequences results in the inactivation of the polyhedron gene and production of non-occluded recombinant virus (i.e., virus lacking the proteinaceous coat coded for by the polyhedron gene). These recombinant viruses are then used to infect *Spodoptera frugiperda* cells in which the inserted gene is expressed (e.g., U.S. Pat. No. 4,215,051).

Examples of useful mammalian host cell lines are VERO and HeLa cells, Chinese hamster ovary (CHO) cell lines, W138, BHK, COS-7, 293, HepG2, NIH3T3, RIN and MDCK cell lines. In addition, a host cell may be chosen that modulates the expression of the inserted sequences, or modifies and processes the gene product in the specific fashion desired. Such modifications (e.g., glycosylation) and processing (e.g., cleavage) of protein products may be important for the function of the encoded protein.

Different host cells have characteristic and specific mechanisms for the post-translational processing and modification of proteins. Appropriate cell lines or host systems can be chosen to ensure the correct modification and processing of the foreign protein expressed. Expression vectors for use in mammalian cells ordinarily include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g., the adenovirus late promoter; the vaccinia virus 7.5K promoter). Further, it is also possible, and may be desirable, to utilize promoter or control sequences normally associated with the desired gene sequence, provided such control sequences are compatible with the host cell systems.

A number of viral based expression systems may be utilized, for example, commonly used promoters are derived from polyoma, Adenovirus 2, cytomegalovirus and Simian Virus 40 (SV40). The early and late promoters of SV40 virus are useful because both are obtained easily from the virus as a fragment which also contains the SV40 viral origin of replication. Smaller or larger SV40 fragments may also be used, provided there is included the approximately 250 bp sequence extending from the HindIII site toward the BglI site located in the viral origin of replication.

In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing proteins in infected hosts.

Specific initiation signals may also be required for efficient translation of the claimed isolated nucleic acid coding sequences. These signals include the ATG initiation codon and adjacent sequences. Exogenous translational control signals, including the ATG initiation codon, may additionally need to be provided. One of ordinary skill in the art would readily be capable of determining this need and providing the necessary signals. It is well known that the initiation codon must be in-frame (or in-phase) with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements or transcription terminators.

In eukaryotic expression, one will also typically desire to incorporate into the transcriptional unit an appropriate polyadenylation site if one was not contained within the original cloned segment. Typically, the poly A addition site is placed about 30 to 2000 nucleotides "downstream" of the termination site of the protein at a position prior to transcription termination.

For long-term, high-yield production of recombinant proteins, stable expression is preferred. For example, cell lines that stably express constructs encoding proteins may be engineered. Rather than using expression vectors that contain viral origins of replication, host cells can be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1-2 days in an enriched medium, and then are switched to a selective medium. The selectable marker in the recombinant plasmid confers resistance to the selection and allows cells to stably integrate the plasmid into their chromosomes and grow to form foci, which in turn can be cloned and expanded into cell lines.

A number of selection systems may be used, including, but not limited, to the herpes simplex virus thymidine kinase, hypoxanthine-guanine phosphoribosyltransferase and adenine phosphoribosyltransferase genes, in tk⁻, hgprt⁻ or aprt⁻ cells, respectively. Also, antimetabolite resistance can be used as the basis of selection for dhfr, which confers resistance to methotrexate; gpt, which confers resistance to mycophenolic acid; neo, which confers resistance to the aminoglycoside G-418; and hygro, which confers resistance to hygromycin. It is appreciated that numerous other selection systems are known in the art that are similarly operable in the present invention.

It is contemplated that the isolated nucleic acids of the disclosure may be "overexpressed", i.e., expressed in increased levels relative to its natural expression in cells of its indigenous organism, or even relative to the expression of other proteins in the recombinant host cell. Such overexpression may be assessed by a variety of methods, including radio-labeling and/or protein purification. However, simple and direct methods are preferred, for example, those involving SDS/PAGE and protein staining or immunoblotting, followed by quantitative analyses, such as densitometric scanning of the resultant gel or blot. A specific increase in the level of the recombinant protein or peptide in comparison to the level in natural human cells is indicative of overexpression, as is a relative abundance of the specific protein in relation to the other proteins produced by the host cell and, e.g., visible on a gel.

A nucleic acid of this invention can be in a cell, which can be a cell expressing the nucleic acid whereby a peptide of this invention is produced in the cell. In addition, the vector of this invention can be in a cell, which can be a cell expressing the nucleic acid of the vector whereby a peptide of this invention is produced in the cell. It is also contemplated that the nucleic acids and/or vectors of this invention can be present in a host animal (e.g., a transgenic animal) which expresses the nucleic acids of this invention and produces the peptides of this invention.

The nucleic acid encoding the peptides of this invention can be any nucleic acid that functionally encodes the peptides of this invention. To functionally encode the peptides (i.e., allow the nucleic acids to be expressed), the nucleic acid of this invention can include, for example, expression control sequences, such as an origin of replication, a promoter, an enhancer and necessary information processing sites, such as ribosome binding sites, RNA splice sites, polyadenylation sites and transcriptional terminator sequences.

Expression control sequences include promoters derived from metallothionine genes, actin genes, immunoglobulin genes, CMV, SV40, adenovirus, bovine papilloma virus, etc. A nucleic acid encoding a selected peptide can readily be determined based upon the genetic code for the amino acid sequence of the selected peptide and many nucleic acids will encode any selected peptide. Modifications in the nucleic acid sequence encoding the peptide are also contemplated. Modifications that can be useful are modifications to the sequences controlling expression of the peptide to make production of the peptide inducible or repressible as controlled by the appropriate inducer or repressor. Such methods are standard in the art. The nucleic acid of this invention can be generated by means standard in the art, such as by recombinant nucleic acid techniques and by synthetic nucleic acid synthesis or in vitro enzymatic synthesis.

An inventive peptide of the present invention is optionally modified to increase its immunogenicity. In a non-limiting example, the antigen is coupled to chemical compounds or immunogenic carriers, provided that the coupling does not interfere with the desired biological activity of either the antigen or the carrier. For a review of some general considerations in coupling strategies, see Antibodies, A Laboratory Manual, Cold Spring Harbor Laboratory, ed. E. Harlow and D. Lane (1988). Useful immunogenic carriers known in the art, include, without limitation, keyhole limpet hemocyanin (KLH); bovine serum albumin (BSA), ovalbumin, PPD (purified protein derivative of tuberculin); red blood cells; tetanus toxoid; cholera toxoid; agarose beads; activated carbon; or bentonite. Useful chemical compounds for coupling include, without limitation, dinitrophenol groups and arsonilic acid.

The inventive polypeptide may also be modified by other techniques, illustratively including denaturation with heat and/or SDS.

In another aspect, the invention provides a multi-component vaccine. Optionally, a multi-component vaccine contains more than one immunogen. An inventive vaccine may contain 2, 3, 4, 5, 6, 7, 8, 9, 10, or more immunogens in a single vaccine. Optionally, a first immunogen is a peptide corresponding to amino acid position 301 to amino acid position 330 of SEQ ID NO: 1, a fragment thereof, or an analogue thereof. Optionally, a first immunogen is a peptide corresponding to amino acid position 41 to amino acid position 70 of SEQ ID NO: 1, a fragment thereof, or an analogue thereof. Optionally, a first immunogen is a peptide corresponding to amino acid position 121 to amino acid position 150 of SEQ ID NO: 1, a fragment thereof, or an analogue thereof. Optionally, a first immunogen is a peptide corresponding to amino acid position 321 to amino acid position 350 of SEQ ID NO: 1, a fragment thereof, or an analogue thereof. Optionally, a first immunogen is a peptide corresponding to amino acid position 421 to amino acid position 450 of SEQ ID NO: 1, a fragment thereof, or an analogue thereof. Optionally, a first immunogen is a peptide corresponding to amino acid position 541 to amino acid position 570 of SEQ ID NO: 1, a fragment thereof, or an analogue thereof. Optionally, a first immunogen is a peptide corresponding to amino acid position 541 to amino acid position 570 of SEQ ID NO: 1, a fragment thereof, or an analogue thereof. Optionally, a first immunogen is a peptide corresponding to amino acid position 561 to amino acid position 590 of SEQ ID NO: 1, a fragment thereof, or an analogue thereof. Optionally, a first immunogen is a peptide corresponding to amino acid position 641 to amino acid position 670 of SEQ ID NO: 1, a fragment thereof, or an analogue thereof. It is appreciated that any of the aforementioned modifications, mutations, or alterations stated herein or otherwise known in the art are operable as to the inventive immunogens of the present invention.

Optionally, an inventive vaccine contains an adjuvant. Suitable adjuvants illustratively include dimethyl dioctadecyl-ammonium bromide (DDA); monophosphoryl lipid A (MPL); LTK63, lipophilic quaternary ammonium salt-DDA, DDA-MPL, aluminum salts, aluminum hydroxide, aluminum phosphate, potassium aluminum phosphate, Montanide ISA-51, ISA-720, microparticles, immunostimulatory complexes, liposomes, virosomes, virus-like particles, CpG oligonucleotides, cholera toxin, heat-labile toxin from *E. coli*, lipoproteins, dendritic cells, IL-12, GM-CSF, nanoparticles illustratively including calcium phosphate nanoparticles, combination of soybean oil, emulsifying agents, and ethanol to form a nanoemulsion; AS04, ZADAXIN, or combinations thereof.

The peptide vaccine is optionally delivered as naked polypeptide, in aqueous solution, in an emulsion, or in other suitable delivery composition. In some embodiments, the invention is delivered as a vaccine or as a vaccine component of a pharmaceutical package. Optionally, a peptide (or multiple peptides) is present in an emulsion including one or more emulsification agents. In some embodiments, a multicomponent vaccine is emulsified. In some embodiments a single subunit vaccine is emulsified. Suitable emulsification agents illustratively include supramolecular biovectors (SMBV), nanoparticles such as described by Major, M, et al, *Biochim. Biophys. Acta*, 1997; 1327:32-40, De Migel, I, et al, *Pharm. Res.*, 2000; 17:817-824, U.S. Pat. Nos. 6,017,513, 7,097,849, 7,041,705, 6,979,456, 6,846,917, 6,663,861, 6,544,646, 6,541,030, 6,368,602, Castignolles, N., et el, *Vaccine*, 1996; 14:1353-1360, Prieur, E., et al, *Vaccine*, 1996; 14:511-520, Baudner B, et al, *Infect Immun*, 2002; 70:4785-4790; Liposomes such as described by El Guink et al., *Vaccine*, 1989; 7:147-151, and in U.S. Pat. No. 4,196,191; or other agents known in the art. Agents suitable for use are generally available from Sigma-Aldrich, St. Louis, Mo. The emulsification agent is optionally a dimethyl dioctadecyl-ammonium bromide. Optionally the adjuvant is monophosphoryl lipid A.

Suitable pharmaceutically acceptable carriers facilitate administration of the immunogens are physiologically inert and/or nonharmful. Carriers may be selected by one of skill in the art. Exemplary carriers include sterile water or saline, lactose, sucrose, calcium phosphate, gelatin, dextran, agar, pectin, peanut oil, olive oil, sesame oil, and water. Additionally, the carrier or diluent may include a time delay material, such as glycerol monostearate or glycerol distearate alone or with a wax. In addition, slow release polymer formulations can be used.

Optionally, the inventive composition may also contain conventional pharmaceutical ingredients, such as preservatives, or chemical stabilizers. Suitable ingredients operable herein include, for example, casamino acids, sucrose, gelatin, phenol red, N-Z amine, monopotassium diphosphate, lactose, lactalbumin hydrolysate, and dried milk.

Immunological compositions and other pharmaceutical compositions containing the peptide(s) described herein are included within the scope of the present invention. One or more of these compositions can be formulated and packaged, alone or in combination, using methods and materials known to those skilled in the art for vaccines. The immunological response may be therapeutic or prophylactic and may provide antibody immunity or cellular immunity such as that produced by T lymphocytes such as cytotoxic T lymphocytes or $CD4^+$ T lymphocytes.

The inventive vaccines may be administered with an adjuvant. Optionally, an adjuvant is alum (aluminum phosphate or aluminum hydroxide). Chemically defined preparations such as muramyl dipeptide, monophosphoryl lipid A, phospholipid conjugates, encapsulation of the conjugate within a proteoliposome, and encapsulation of the protein in lipid vesicles are also operable with the present invention.

Suitable methods of administration include, but are not limited to intramuscular, intravenous, intranasal, mucosal, oral, parenteral, intravaginal, transdermal, via aerosol delivery or by any route that produces the desired biological effect or immune response.

A vaccine of the invention is optionally packaged in a single dosage for immunization by parenteral (i.e., intramuscular, intradermal or subcutaneous) administration or nasopharyngeal (i.e., intranasal) administration. The vaccine is optionally delivered by inhalation. The vaccine is optionally combined with a pharmaceutically acceptable carrier to facilitate administration. The carrier is usually water or a buffered saline, with or without a preservative. The vaccine may be lyophilized for resuspension at the time of administration or in solution.

Optional microencapsulation of the inventive vaccine will also provide a controlled release. A number of factors contribute to the selection of a particular polymer for microencapsulation. The reproducibility of polymer synthesis and the microencapsulation process, the cost of the microencapsulation materials and process, the toxicological profile, the requirements for variable release kinetics and the physicochemical compatibility of the polymer and the antigens are all factors that may be considered. Examples of useful polymers illustratively include polycarbonates, polyesters, polyurethanes, polyorthoesters polyamides, poly(d,l-lactide-co-glycolide) (PLGA) and other biodegradable polymers.

The inventive vaccine may additionally contain stabilizers such as thimerosal (ethyl(2-mercaptobenzoate-S)mercury sodium salt) (Sigma Chemical Company, St. Louis, Mo.) or physiologically acceptable preservatives.

Additional, a human or other animal may be treated for anthrax infection by administering an effective amount of an immunogen of the invention. An "effective amount" is optionally between about 0.05 to about 1000 µg/mL of an immunogen. A suitable dosage may be about 1.0 mL of such an effective amount. Such a composition may be administered 1-3 times per day over a 1 day to 12 week period. However, suitable dosage adjustments may be made by the attending physician or veterinarian depending upon the age, sex, weight and general health of the subject. Such a composition is optionally administered parenterally, optionally intramuscularly or subcutaneously. However, it may also be formulated to be administered by any other suitable route, including orally or topically.

Embodiments of inventive compositions and methods are illustrated in the following examples. These examples are provided for illustrative purposes and are not considered limitations on the scope of inventions.

EXAMPLES

Example 1

Synthesis of Peptides

Fmoc synthesis is used to prepare 37 N-terminally biotinylated peptides of 30 amino acid (AA) residues each, overlapping by 10 AA representing sequences of PA (SEQ ID NO: 1). The peptide representing the C-terminus of SEQ ID NO: 1 is made as the free acid. All sequences are Fmoc synthesized as C-terminal amides, HPLC-purified, and prepared as trifluoroacetic acid salts. Peptides are captured on streptavidin coated beads (2 µg/ml).

Example 2

Screening of Sera from Rhesus Macaques, Rabbits and Human Subjects Immunized with a Vaccine Including PA Sequences for Acquired Immunity AVA vaccine (BIOTHRAX), and purified rPA (50 µg dose) vaccine (BEI Resources 10801 University Boulevard, Manassas, Va.) are obtained from Emergent BioSolutions, Rockville, Md. New Zealand white rabbits were vaccinated with an undiluted human dose or 1:10 or 1:20 dilution at 0, 4, 26 weeks with 0.5 ml of either AVA or purified rPA. Rhesus macaques are vaccinated by intramuscular injection with 50

μg of rPA at 0, 2, 4, 8, 12, 16, 20 weeks. Macaques in one study were vaccinated with AVA at 0, 4, 26 weeks with undiluted or diluted human dose of AVA (1:5, 1:10, 1:20 and 1:40). All dilutions are in saline. As a control, animals are vaccinated with an equal volume of saline at the same intervals.

Ten human subjects are vaccinated with AVA at the recommended dose and schedule of administration following the regimen at the time of the study with administration at 0-2-4 weeks and 6-12-30-42 months with annual boosters.

Whole blood is obtained from human, macaque, and rabbit subjects by venipuncture. All blood is collected into tubes in the absence of an anticoagulant. Tubes are allowed to incubate on the bench top for 45 minutes to induce clot formation. The resulting serum is separated by centrifugation at 2000×g for 15 minutes and aspirated as the supernatant. All samples are either assayed immediately or stored at −80° C. until assay.

Peptide-Specific Enzyme-Linked Immunosorbent Assay (ELISA)

IMMULON 2 HB microtiter plates (Thermo Labsystems, Franklin, Mass.) were coated with streptavidin (Promega, Madison, Wis.) at 2 μg/ml and purified rPA (BEI Resources, Manassas, Va.) in control wells (2 μg/ml) in 0.01 M phosphate buffered saline (PBS) pH 7.4 (Invitrogen, Carlsbad, Calif.). Plates were incubated overnight (16-24 hours) at +4° C. and then washed 3 times with PBS containing 0.1% Tween-20, pH 7.4 (ELISA Wash Buffer). The plate was divided into two equal parts (four rows in each) and each part was coated with peptides at 1 μg/ml (one peptide per well), incubated overnight (16-24 hours) at +4° C. and then washed 3 times with ELISA Wash Buffer. Each well was loaded with 1:50 dilution of test serum (top portion of the plate) or negative control (bottom portion of the plate) diluted in PBS containing 5% Skim Milk and 0.5% Tween-20, pH 7.4 (Serum Diluent). Plates were incubated for 60 min at 37° C. and washed 3 times with ELISA wash buffer. 100 μl of species specific anti-IgG conjugated to horseradish peroxidase was added to all wells and incubated at 37° C. for 60 min. Plates were washed 3 times and 100 μl of ABTS Microwell Peroxidase Substrate System (Kirkegaard and Perry Laboratories, Gaithersburg, Md.) was added to all wells. After 30 min incubation at 37° C. 100 μl of ABTS Peroxidase Stop Solution (Kirkegaard and Perry Laboratories, Gaithersburg, Md.) was added to each well and plates were read within 30 min with a Microplate Spectrophotometer Bio-Tek PowerWave™ (Bio-Tek Instruments, Inc., Winooski, Vt.) at a wavelength of 405 nm with a 490 nm reference. Assay endpoints were reported as OD values. A peptide was considered antigenic if its Optical Density (OD) value was greater than the mean OD plus 3 Standard Deviations (SD) of controls.

The reactivity of serum from three different pools of vaccinated Rhesus macaques are illustrated in FIG. 1. Additional testing is illustrated in FIGS. 6 and 7. At least one peptide representing amino acid sequence from each of the four domains of PA is a target for PA specific IgG in Rhesus macaques. Particularly strong reactivity is observed in domain 2 between amino acids 301 and 330 as well as in various locations in domain 4. Macaque AVR817 is a negative control and demonstrates baseline activity throughout PA.

Interestingly, similar profiles of reactivity are observed in sera from rabbits and humans vaccinated with AVA. FIG. 2 demonstrates strong reactivity in domain 2 for peptides corresponding to residues 301-330 of mature PA. Rabbits also show strong reactivity in a range of domain 3 regions and domain 4 regions. Humans show the most restricted reactivity of the three species, but the overall regions of reactivity are similar with high reactivity in domain 2 at amino acids 301-330 and in domain 4.

The seroreactivity is independent on the type of peptide or vaccine used to vaccinate both humans and rhesus macaques. FIG. 4 illustrates the reactivity in sera from rhesus macaques vaccinated either with AVA or rPA and show highly correlative reactivity. Additionally, the addition of four administrations in macaques to a total of 7 does not alter the reactivity indicating that full immunity is observed after three administrations. (FIG. 5)

Overall, vaccination with rPA or AVA vaccines produces a robust immune response with the generation of antibodies to several regions of PA encompassing domains 1-4.

Example 3

Production of Peptide Vaccines

Fmoc synthesis is used to prepare 11 peptide vaccines. The peptide vaccines have the following sequences describing the amino acid numbering of SEQ ID NO: 1: the calcium ion chelating residues in the $1\alpha_1$ and $1\beta_{13}$ strands (AA181-210) (DGIPDSLEVEGYTVDVKNKRTFLSPWISNI (SEQ ID NO: 4)); $1\beta_{13}$, $1\alpha_2$, $1\beta_{14}$ (AA201-230) (TFLSPWISNIHEKKGLTKYKSSPEKWSTAS (SEQ ID NO: 5)); $1\alpha_3$ and $1\alpha_4$ (AA 221-250) (SSPEKWSTASDPYSDFEKVTGRIDKNVSPE (SEQ ID NO: 6)); and $1\alpha_4$ and $2\beta_1$ (AA241-270) (GRIDKNVSPEARHPLVAAYPIVHVDMENII SEQ ID NO: 7)); the chymotrypsin sensitive loop $2\beta_2$-$2\beta_3$ (AA 301-330) (SEVHGNAEVHASFFDIGGSVSAGFSNSNSS (SEQ ID NO: 3)); $2\beta_3$ and $2\alpha_1$ (AA 321-350) (SAGFSNSNSSTVAIDHSLSLAGERTWAETM (SEQ ID NO: 8)); $2\alpha_1$, $2\beta_4$ and $2\beta_5$ (AA341-370) (AGERTWAETMGLNTADTARLNANIRYVNTG (SEQ ID NO: 9); $2\beta_6$ and $2\beta_7$ (AA361-390) (NANIRYVNTGTAPIYNVLPTTSLVLGKNQT (SEQ ID NO: 10); $2\beta_{10}$, $2\beta_{11}$, $2\alpha_2$ and $2\beta_{12}$ (AA421-450) (LNAQDDFSSTPITMNYNQFLELEKTKQLRL (SEQ ID NO: 11)); $2\beta_{13}$ in domain 2, $3\alpha_3$, $3\alpha_4$ (AA 561-590) (NIKNQLAELNVTNIYTVLDKIKLNAKMNIL (SEQ ID NO: 12)); $3\beta_7$, $3\beta_8$ (AA581-610) (IKLNAKMNILIRDKRFHYDRNNIAVGADES (SEQ ID NO: 13)); AA41-70 GDLSIPSSELENIPSENQYFQSAIWSGFIK (SEQ ID NO: 14); AA401-430 LSQILAPNNYYPSKNLAPIALNAQDDFSST (SEQ ID NO: 15); AA641-670 GYIVEIEDTEGLKEVINDRYDMLNISSLRQ (SEQ ID NO: 16); and AA681-710 peptide 35 YNDKLPLYISNPNYKVNVYAVTKENTIINP (SEQ ID NO: 17). Control mice are immunized with a scrambled peptide of 30 amino acids in length. All sequences are Fmoc synthesized as C-terminal amides, HPLC-purified, and prepared as trifluoroacetic acid salts.

The immunization studies in mice are performed in accordance with federal and institutional guidelines. Female BALB/c mice, 6-8 weeks old, 20-50 g weight (The Jackson Laboratory, Bar Harbor, Me.) were immunized with 3 injections of 20 μg of peptides in Sigma Adjuvant System® (Sigma-Aldrich®, St. Louis, Mo.). Blood collected 14 days after the third injection by cardiac puncture. Sera were stored at −20° C.

For detection of PA and anti-peptide specific antibodies, 96-well microtiter ELISA plates are coated with 100 μl/well of PA or one of each peptide at a concentration of 2.0 μg/ml in PBS, pH 7.4. The plates are stored overnight at 4° C. The serum samples from the mouse are serially diluted (1:100 to 1:128,000). Plates are incubated with 100 μl of diluted serum samples for 1 h at 37° C. followed by washing with PBS- Tween. The plates are then incubated for 1 h at 37° C. with 100 μl of HRP-conjugated goat anti-mouse IgG (1:5,000 dilution of 1-mg/ml stock). ABTS Microwell Peroxidase Substrate System (Kirkegaard and Perry Laboratories, Gaithersburg, Md.) was used as the substrate and the reaction was stopped by adding 100 μl of Stop Solution (Kirkegaard and Perry Laboratories, Gaithersburg, Md.). The plates were read within 30 min with a Microplate Spectrophotometer Bio-Tek PowerWave™ (Bio-Tek Instruments, Inc., Winooski, Vt.) at a wavelength of 405 nm with a 490 nm reference.

Several of the immunogens elicit the production of antibodies in mice with the exception of the control peptide that is at background levels.

The same immunogens may be used to vaccinate humans. The immunogens may be conjugated to KLH or other antigenicity enhancing agent. Serum samples will be collected at the time of each human subject administration. A profile of the presence of antibodies to PA and the level of antibodies in each subject's serum will be determined by ELISA. Human subjects are expected to show little antibody production after the first and second administrations indicating that at least one additional booster immunization is required to develop required immunity. The levels of antibodies are expected to be sufficiently present after three administrations. Subsequent administrations should not significantly increase the level of serum antibodies. Thus, three administrations is expected to be sufficient to confer immunity in most human subjects.

Example 4

Anthrax Toxin Neutralization

Sera from immunized mice as in Example 3 are tested for neutralization in a macrophage cytotoxicity assay. The real-time cell analyzer (RTCA, Roche Applied Science, Indianapolis, Ind.) was used to monitor the LTx induced cell intoxication dynamics and measure the antibody toxin neutralization activity (ED50) and toxin potency (IC50) via measurement of the cell index (CI) changes. CI is a parameter describing electronic impendence, which corresponds to the number of cells attached to the bottom of microelectrode-embedded microplate (E-plate, Roche) well. Anthrax LTx intoxicated J774 cells and caused cell death, thus declining the CI values. J774 cells were seeded in 96-well E-plate at a density of $5 \times 10^4$/well. Cell plate was placed on the RT-CES device station and incubated at 37° C. with 5% $CO_2$ atmosphere for 17-20 hours prior to adding toxin or biological samples. Antibody toxin neutralization activity to LTx was measured by mixing a fixed concentration of LTx, at 50 ngPA83/40 ngLF/ml or 150 ngPA63/100 ngLF/ml with serial diluted antibody solutions. The mixture of Ab-LTx was incubated at 37° C. for 30 min, and then was transferred to E-plate. The cell plate was incubated at 37° C. for additional 24 hours. CI was recorded in every 5 minutes for 6 hours and additional 18 hour in one hour interval.

Example 5

Correlates of Protection

Seroreactivity of peptides was determined by streptavidin-capture enzyme immunosorbent assay. A peptide was considered antigenic if its Optical Density (OD) value was greater than the mean OD plus 3 Standard Deviations (SD) of control animal serum's reactivity for that peptide. Fisher's exact test was used for comparison of anti-peptide antibody responses in survivors vs. non-survivors. Predictive measures of survival probability included logistic regression analysis of immunoreactivity for each peptide and for selected groups of peptides and Area under the curve for Receiver Operating Characteristic (ROC) analysis.

The seroreactivity of individual peptides from rhesus macaques are independently analyzed for determination of degree of protection conferred by antibodies to individual regions of PA. Rhesus macaques previously vaccinated by 3 intramuscular injection of AVA at 0, 4, 26 wk. of undiluted AVA (n=18), or saline-diluted AVA (1/5, n=16; 1/10, n=25; 1/20, n=21 and 1/40, n=15). All dilutions are in saline. As a control, animals are vaccinated with an equal volume of saline at the same intervals.

B. anthracis Ames strain was prepared and characterized as per established procedures. Anesthetized rhesus macaques were challenged via head-only exposure in a class III biosafety cabinet with approximately with 200-400 LD50 of aerosolized B. anthracis equivalents of B. anthracis Ames spores (approximately $1.7 \times 10^7$ to $2.2 \times 10^7$ spores, where $1 \times LD_{50}$ equals 55,000 spores or CFU). The spore dose corresponds to that which has been used to yield high infection rates (Viteri et al, J. Infect. Dis., 2009; 199336-341). Aerosol exposure time was adjusted so that each animal inhaled the required cumulative volume of air to attain the targeted dose, assuming 100% retention of the inhaled dose. Exposure times ranged from 10 to 30 min, and animals were anesthetized for the entire period to minimize stress. Actual total spore exposure doses ranged from 308 to 460 $LD_{50}$ equivalents of B. anthracis Ames spores (geometric mean±percent SE=378±8 $LD_{50}$).

Survivors and non-survivors are analyzed for the presence of absence of antibodies to each predetermined region of PA as described in Example 2. A Fisher's exact test was used for comparison of immune responses to peptides responses from the survivors vs. non-survivors. A Logistic Regression Analysis was performed on each peptide and groups of peptides as a variable for predicted probability of survival. Receiver Operating Characteristic (ROC) area under the curve was used as a measure of the accuracy of survival probability estimates.

Figure 8:
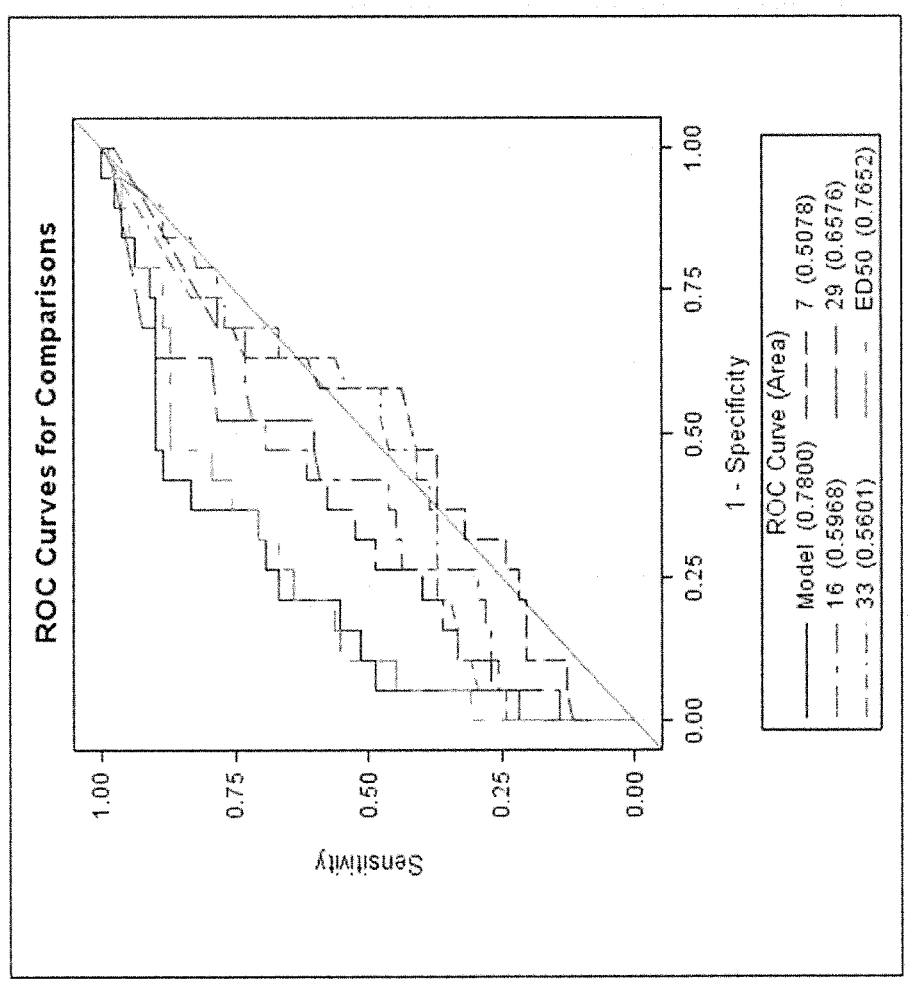
FIG. 8 represents the prediction of survival probability based on frequency response over 10% using selected peptides 7, 16, 29, 33.

FIG. 8 illustrates a Logistic Regression Analysis with a Receiver Operating Characteristic (ROC) area under the curve as a measure of the prediction accuracy of survival for each individual peptide number 7, 16, 29, and 33 as well as the group (Model). These are compared to TNA antibody level (ED50) alone as a correlate of protection. It is observed that the ED50 demonstrates a ROC value of 0.7652 alone versus 0.7800 of the model. Individually, each of the peptides presented has a lower prediction accuracy of survival than the model. The group of peptides, however, when used in combination (Model) shows slightly better prediction accuracy of survival (ROC=0.7800) than ED50.

Figure 9:
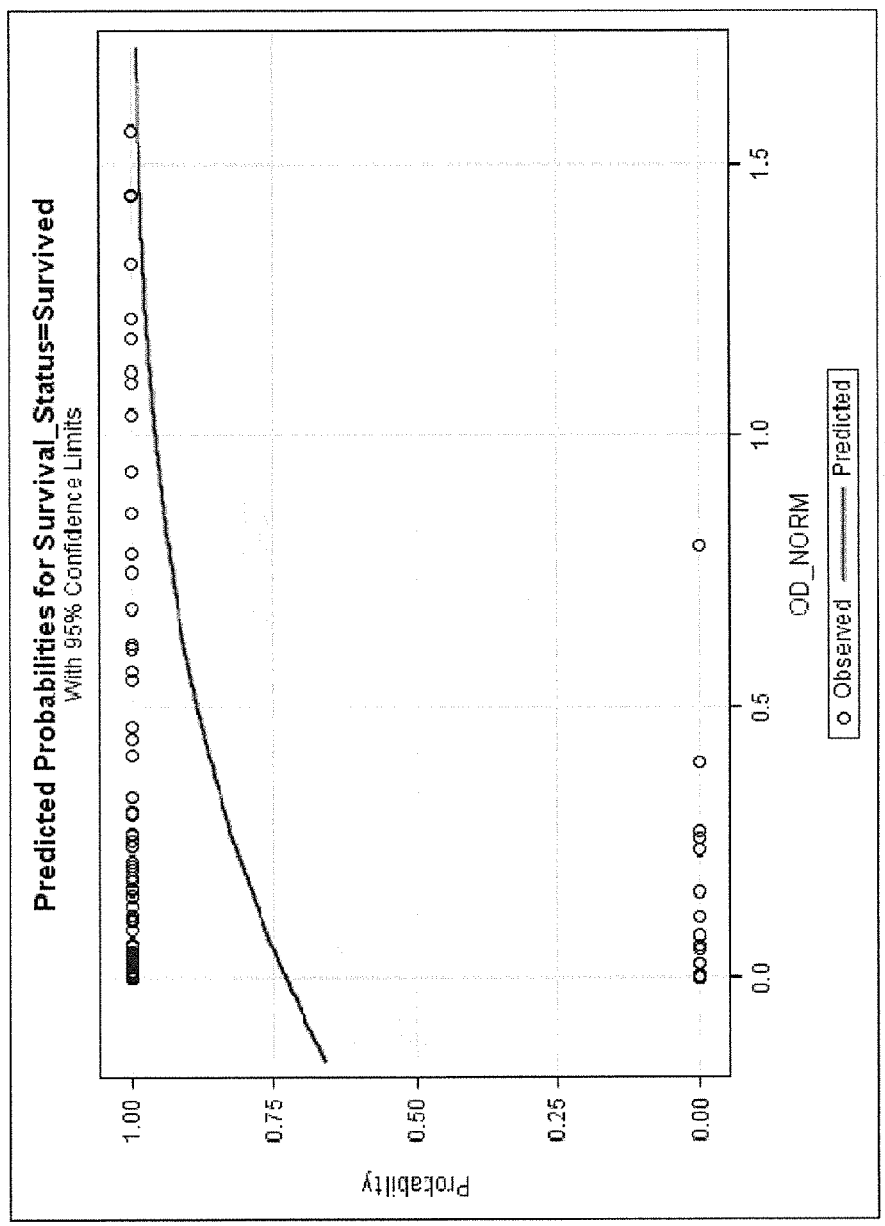
FIG. 9 represents a prediction of survival probability based on the Fisher's exact test (OD value) for peptide 29 in survivor and non-survivor macaques illustrating a positive correlation to survival.
Figure 10:
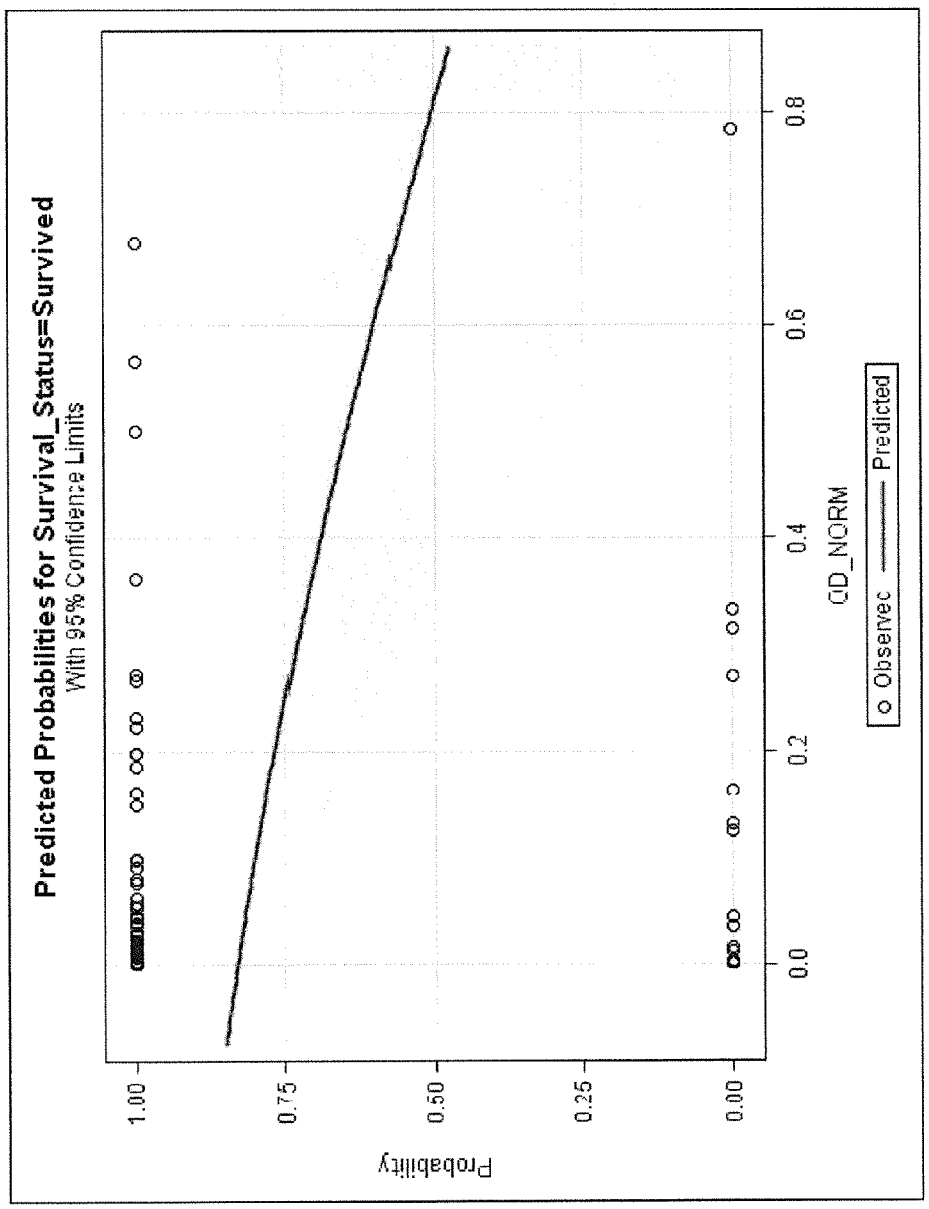
FIG. 10 represents a prediction of survival probability based on the Fisher's exact test (OD value) for peptide 35 in survivor and non-survivor macaques illustrating a negative correlation to survival.
Figure 11:
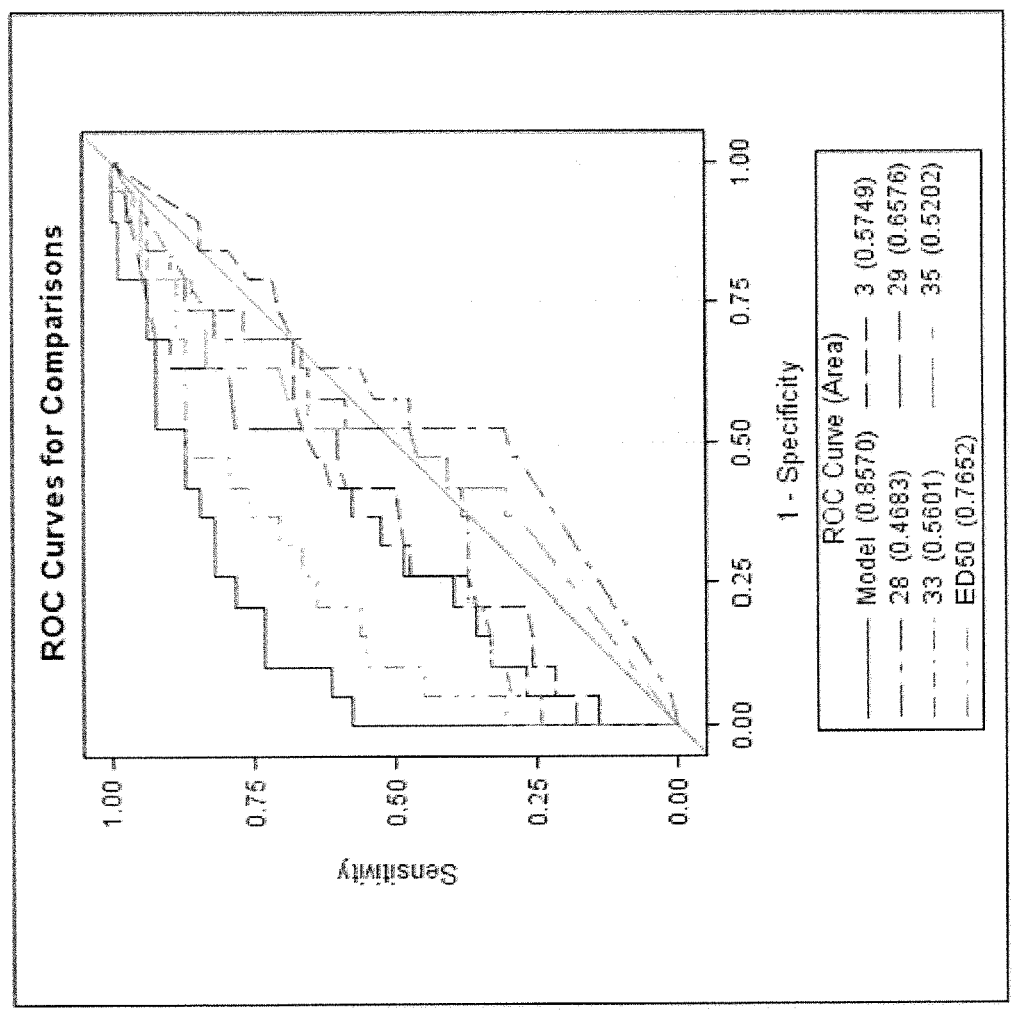
FIG. 11 illustrates a prediction of survival probability based on the significant likelihood ratio p value (<0.05) of individual peptides' immune response between survivor and non-survivor macaques using selected peptides 3, 28, 29, 33, and 35.
Figure 12:
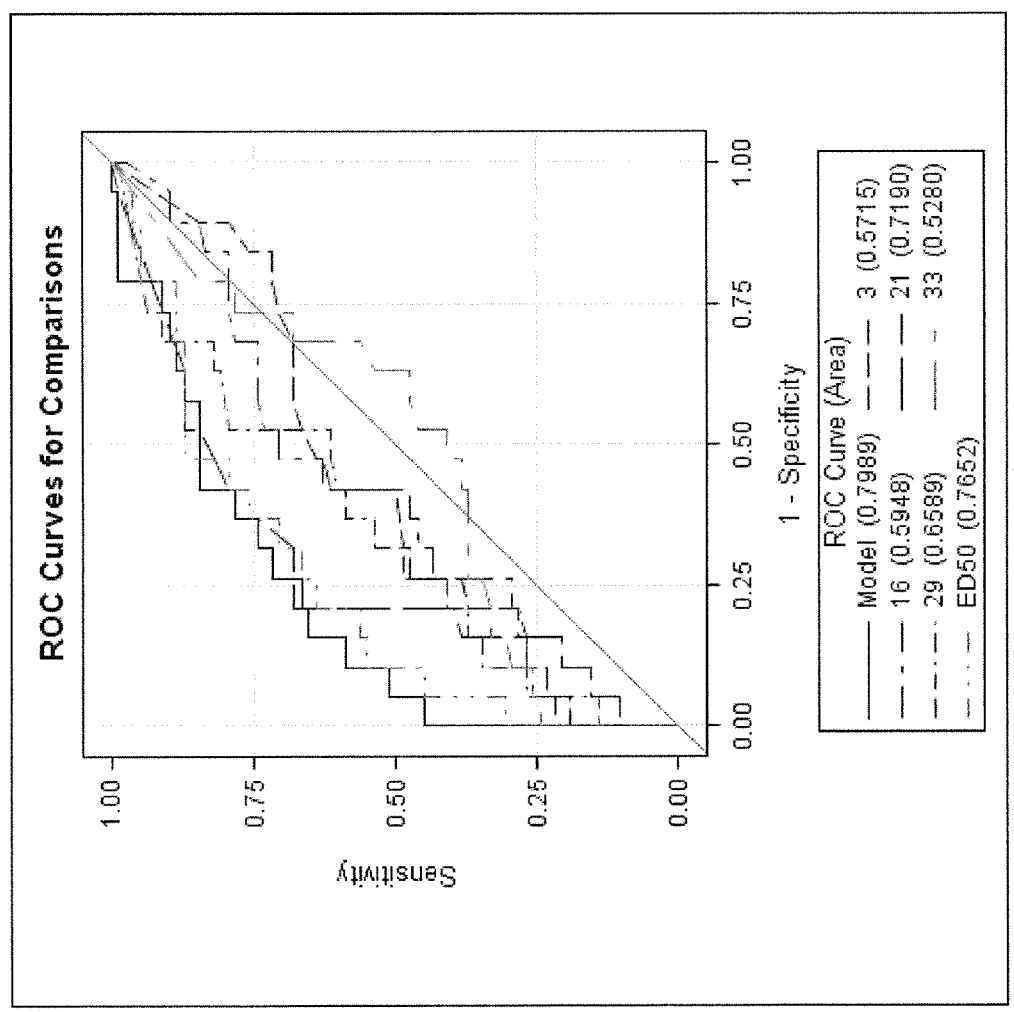
FIG. 12 illustrates a prediction of survival probability based on the peptides selected from R package pensim using selected peptides 3, 16, 21, 29, and 33.

FIG. 9 illustrates a survival curve for peptide 29 illustrating a positive correlation to survival. Interestingly, peptide 35 illustrates a negative correlation to survival as is illustrated in FIG. 10. This indicates that for this peptide, the presence of an antibody to an epitope in the predefined region represented by the peptide suggests decreased survival. This result is interesting in that the reactivity of PA in this region is virtually absent as is observed in FIG. 7.

Logistic regression analyses are carried out on individual peptides 3, 7, 16, 28, 29, 33, and 35 as well as the entire group as a model illustrate that antibodies to each of the peptides individually show less correlation to survival than total IgG as a correlate of protection. However, when these peptides are modeled as a group, anti-PA IgG to these sequences enhance the prediction accuracy of survival against anthrax in rhesus macaques with ROC area under the curve of 0.8570. This result is higher than the 0.7652 ROC value when only ED50 is used as the immune correlate. This improves the survival prediction accuracy of vaccine induced anti-PA IgG and TNA responses as immune correlates of protection against inhalation anthrax. The following five methods of peptides selection were used: 1) Method 1: (R-Elasticnet) Logistic regression model using elastic net penalty, which is a combination of LASSO and ridge regression penalties; 2) Methods 2: (R-glmnet) Generalized linear modeling using elastic net penalties; 3) Method 3: (Response Frequency) 10% higher frequency response above the OD values of non-survivors; 4) Method 4: (Fisher's Exact Test) Contingency analysis tables used in preliminary data analysis where n<30 compared anti-peptide antibody responses in OD values in survivors vs. non-survivors; 5) Method 5: (R-pensim) Penalized mutlivariate regression using elastic net penalty. SAS® version 9.3 (SAS Institute Inc. Cary, N.C. USA) procedure PROC LOGISTIC was used to model each of the group of peptides to obtain ROC curves and maximum likelihood ratio p values. Area under the ROC curve was used as a measure of predictive accuracy of the models.

Table 2 illustrates logistic regression on group of peptides the ROC analyses and statistical likelihood for each of these peptides.

TABLE 2 prediction of survival probability based on the significant likelihood ratio p value (<0.05) of individual peptides' immune response between survivor and non-survivor macaques using selected peptides 3, 7, 16, 21, 28, 29, 33, 35.

| Peptide | AA range | Domain | P value | ROC value |
|---|---|---|---|---|
| 3 | 41-70 | I | 0.057 | 0.5749 |
| 7 | 121-150 | I | 0.2961 | 0.5078 |
| 16 | 301-330 | II | 0.0386 | 0.5968 |
| 21 | 401-430 | II | 0.0257 | 0.7274 |
| 28 | 541-570 | III | 0.2851 | 0.4683 |
| 29 | 561-590 | III | 0.0272 | 0.6576 |
| 33 | 641-670 | IV | 0.0243 | 0.5601 |
| 35 | 681-710 | IV | 0.2107 | 0.5202 |

All peptides show statistical significance in antibody responses to selected regions of PA between AVA vaccinated NHP that survived or succumbed to inhalation anthrax with the exception of peptide 3, when analyzed on an individual basis.

The above studies are repeated for all other combinations of peptides with groupings ranging from 2 to 5 peptides. The groupings with the highest ROC are illustrated in Table 3:

TABLE 3

Groups of predefined regions of PA that illustrate the greatest improvement in prediction of probability of survival against inhalational anthrax in rhesus macaques in comparison with prediction of survival based only on ED50 of anti-PA IgG with an ROC of 0.7652.

| Group of Peptides | Receiver Operating Characteristic |
|---|---|
| 3, 28, 29, 33, 35 | 0.8570 |
| 3, 16, 21, 28, 33 | 0.8462 |
| 28, 29, 33, 35 | 0.8428 |
| 28, 35 | 0.8192 |
| 3, 16, 21, 29, 33 | 0.8003 |
| 7, 16, 29, 33 | 0.7800 |
| 29, 33 | 0.7740 |
| 29, 35 | 0.8117 |

It is observed that each grouping includes peptides 33 (AA 641-670) or 35 (681-710) suggesting that epitopes in the regions of these peptides are excellent correlates of protection to complications from exposure to B. anthracis. When used in groupings including other epitopes encompassed in other predefined regions, excellent prediction can be made as to the presence of sufficient protection conferred by prior vaccination. For example, a subject with antibodies to epitopes in peptides 3, 7, 16, 21, 28, 29, and 33 as well as absence of an antibody to an epitope in peptide 35 indicates high likelihood of sufficient vaccine protection. These correlates of protection are independent of the number of times a subject has been vaccinated and may be used to determine if subsequent vaccination is necessary.

Methods involving conventional biological techniques are described herein. Such techniques are generally known in the art and are described in detail in methodology treatises such as Molecular Cloning: A Laboratory Manual, 3rd ed., vol. 1-3, ed. Sambrook et al., Cold Spring Harbor Laboratory Press, Cold Spring Harbor, N.Y., 2001; Current Protocols in Molecular Biology, ed. Ausubel et al., Greene Publishing and Wiley-Interscience, New York, 1992 (with periodic updates); and Short Protocols in Molecular Biology, ed. Ausubel et al., 52 ed., Wiley-Interscience, New York, 2002. Immunological methods (e.g., preparation of antigen-specific antibodies, immunoprecipitation, and immunoblotting) are described, e.g., in Current Protocols in Immunology, ed. Coligan et al., John Wiley & Sons, New York, 1991; and Methods of Immunological Analysis, ed. Masseyeff et al., John Wiley & Sons, New York, 1992.

Methods of producing and screening antibodies are illustratively found in Monoclonal Antibodies: Methods and Protocols, Albitar, M, ed., Humana Press, 2010 (ISBN 1617376469); and Antibodies: A Laboratory Manual, Harlos, E, and Lane, D. eds., Cold Spring Harbor Laboratory Press, 1988 (ISBN-10: 0879693142).

Additional protocols such as PCR Protocols can be found in A Guide to Methods and Applications Academic Press, NY. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification," Methods in Enzymology vol. 182, and other volumes in this series; Current Protocols in Protein Science, John Wiley and Sons, New York, N.Y.; and manufacturer's literature on use of protein purification products known to those of skill in the art.

Various modifications of the present invention, in addition to those shown and described herein, will be apparent to those skilled in the art of the above description. Such modifications are also intended to fall within the scope of the appended claims.

It is appreciated that all reagents are obtainable by sources known in the art unless otherwise specified. Methods of nucleotide amplification, cell transfection, and protein expression and purification are similarly within the level of skill in the art.

REFERENCE LIST

Quinn C P, Sabourin C L, Niemuth N A, Li H, Semenova V A, Rudge T L, Mayfield H J, Schiffer J, Mittler R S, Ibegbu C C, Wrammert J, Ahmed R, Brys A M, Hunt R E, Levesque D, Estep J E, Barnewall R E, Robinson D M, Plikaytis B D, Marano N; AVRP Laboratory Working Group. 2012. Three-Dose Intramuscular Injection Schedule of Anthrax Vaccine Adsorbed Generates Sustained Humoral and Cellular Immune Responses to Protective Antigen and Provides Long-Term Protection against Inhalation Anthrax in Rhesus Macaques. *Clin Vaccine Immunol.* 19:1730-1745.

DeLong E R, DeLong D M, Clarke-Pearson D L. 1988. Comparing the Areas under Two or More Correlated Receiver Operating Characteristic Curves: A Nonparametric Approach, Biometrics: 44: 837-845.

Friedman J, Hastie T, Tibshirani R. 2010. Regularization Paths for Generalized Linear Models via Coordinate Descent. J Stat Softw. 33:1-22.

Waldron L, Pintilie M, Tsao M S, Shepherd F A, Huttenhower C, Jurisica I. 2011. Optimized application of penalized regression methods to diverse genomic data. Bioinformatics. 27:3399-3406.

Patents and publications mentioned in the specification are indicative of the levels of those skilled in the art to which the invention pertains. These patents and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A process of determining if a subject has acquired immunity against B. anthracis infection in a subject comprising:
   obtaining a biological sample from a subject;
   screening said biological sample for the presence or absence of antibodies to one or more predefined regions of Bacillus anthracis protective antigen, at least one of said predefined regions consisting of residues 681-710 of SEQ ID NO: 1; and
   determining subject as having acquired immunity against B. anthracis by the presence of antibodies to one or more of said predefined regions, or determining said subject as lacking acquired immunity against B. anthracis from said screening by the absence of antibodies to one or more of said predefined regions.

2. The process of claim 1 further comprising vaccinating said subject with an anthrax vaccine adsorbed (AVA) vaccine or a B. anthracis protective antigen.

3. The process of claim 1 wherein said predefined region of B. anthracis protective antigen further includes at least one of amino acid region of SEQ ID NO: 1 selected from the group consisting of residues consisting of 41-70, 181-210, 201-230, 221-250, 241-270, 301-330, 321-350, 341-370, 361-390, 421-450, 561-590, 581-610, or 641-670.

4. The process of claim 1 wherein said at least one of said predefined regions of B. anthracis protective antigen consists of amino acid region 561-590 of SEQ ID NO: 1.

5. The process of claim 1 wherein said at least one of said predefined regions of B. anthracis protective antigen consists of amino acid region 401-430 of SEQ ID NO: 1.

6. The process of claim 1 wherein said obtaining is following a first onset time following administration of a first vaccine.

7. The process of claim 2 further comprising a second administering of said vaccine, and obtaining a second biological sample following a second onset time following administration of said second administering of said vaccine;
   screening said second biological sample for the presence or absence of antibodies to one or more of said predefined regions of B. anthracis protective antigen; and
   determining said subject having acquired immunity against B. anthracis from said screening of said second biological sample by the presence of antibodies to one or more of said predefined regions, or determining said subject as lacking acquired immunity against B. anthracis from said screening by the absence of antibodies to one or more of said predefined regions.

8. The process of claim 7 wherein said at least one of said predefined regions of B. anthracis protective antigen consists of amino acid region 681-710 of SEQ ID NO: 1.

9. The process of claim 1 wherein said predefined regions include the regions of residues consisting of 561-590 and 681-710 of SEQ ID NO: 1.

10. The process of claim 1 wherein said predefined regions include the regions of residues consisting of 41-70, 541-570, 561-590, 641-670, and 681-710 of SEQ ID NO: 1.

11. The process of claim 1 wherein said predefined regions include the regions of residues consisting of 41-70, 301-330, 401-430, 541-570, and 641-670 of SEQ ID NO: 1.

12. The process of claim 1 wherein said predefined regions include the regions of residues consisting of 541-570, 561-590, 641-670, and 681-710 of SEQ ID NO: 1.

13. The process of claim 1 wherein said predefined regions include the regions of residues consisting of 541-570 and 681-710 of SEQ ID NO: 1.

14. The process of claim 1 wherein said predefined regions include the regions of residues consisting of 41-70, 301-330, 401-430, 561-590, and 641-670 of SEQ ID NO: 1.

15. The process of claim 1 wherein said predefined regions include the regions of residues consisting of 121-150, 301-330, 561-590, and 641-670 of SEQ ID NO: 1.

16. The process of claim 1 wherein said predefined regions include the regions of residues consisting of 561-590 and 641-670 of SEQ ID NO: 1.

17. The process of claim 1 wherein said predefined regions include the regions of residues consisting of 561-590 and 681-710 of SEQ ID NO: 1.

18. The process of claim 1 wherein said predefined regions include the regions of amino acids consisting of 41-70, 121-150, 181-210, 201-230, 221-250, 241-270, 301-330, 321-350, 341-370, 361-390, 401-430, 421-450, 541-570, 561-590, 581-610, 641-670, and 681-710 of SEQ ID NO: 1.

* * * * *

```
                        SEQUENCE LISTING

<160> NUMBER OF SEQ ID NOS: 17

<210> SEQ ID NO 1
<211> LENGTH: 735
<212> TYPE: PRT
<213> ORGANISM: Bacillus anthracis

<400> SEQUENCE: 1

Glu Val Lys Gln Glu Asn Arg Leu Leu Asn Glu Ser Glu Ser Ser Ser
1               5                   10                  15

Gln Gly Leu Leu Gly Tyr Tyr Phe Ser Asp Leu Asn Phe Gln Ala Pro
            20                  25                  30

Met Val Val Thr Ser Ser Thr Thr Gly Asp Leu Ser Ile Pro Ser Ser
        35                  40                  45

Glu Leu Glu Asn Ile Pro Ser Glu Asn Gln Tyr Phe Gln Ser Ala Ile
    50                  55                  60

Trp Ser Gly Phe Ile Lys Val Lys Lys Ser Asp Glu Tyr Thr Phe Ala
65                  70                  75                  80

Thr Ser Ala Asp Asn His Val Thr Met Trp Val Asp Asp Gln Glu Val
                85                  90                  95

Ile Asn Lys Ala Ser Asn Ser Asn Lys Ile Arg Leu Glu Lys Gly Arg
            100                 105                 110

Leu Tyr Gln Ile Lys Ile Gln Tyr Gln Arg Glu Asn Pro Thr Glu Lys
        115                 120                 125

Gly Leu Asp Phe Lys Leu Tyr Trp Thr Asp Ser Gln Asn Lys Lys Glu
    130                 135                 140

Val Ile Ser Ser Asp Asn Leu Gln Leu Pro Glu Leu Lys Gln Lys Ser
145                 150                 155                 160

Ser Asn Ser Arg Lys Lys Arg Ser Thr Ser Ala Gly Pro Thr Val Pro
                165                 170                 175

Asp Arg Asp Asn Asp Gly Ile Pro Asp Ser Leu Glu Val Glu Gly Tyr
            180                 185                 190

Thr Val Asp Val Lys Asn Lys Arg Thr Phe Leu Ser Pro Trp Ile Ser
        195                 200                 205

Asn Ile His Glu Lys Lys Gly Leu Thr Lys Tyr Lys Ser Ser Pro Glu
    210                 215                 220

Lys Trp Ser Thr Ala Ser Asp Pro Tyr Ser Asp Phe Glu Lys Val Thr
225                 230                 235                 240

Gly Arg Ile Asp Lys Asn Val Ser Pro Glu Ala Arg His Pro Leu Val
                245                 250                 255

Ala Ala Tyr Pro Ile Val His Val Asp Met Glu Asn Ile Ile Leu Ser
            260                 265                 270
```

-continued

```
Lys Asn Glu Asp Gln Ser Thr Gln Asn Thr Asp Ser Gln Thr Arg Thr
                275                 280                 285

Ile Ser Lys Asn Thr Ser Thr Ser Arg Thr His Thr Ser Glu Val His
    290                 295                 300

Gly Asn Ala Glu Val His Ala Ser Phe Phe Asp Ile Gly Gly Ser Val
305                 310                 315                 320

Ser Ala Gly Phe Ser Asn Ser Asn Ser Ser Thr Val Ala Ile Asp His
                325                 330                 335

Ser Leu Ser Leu Ala Gly Glu Arg Thr Trp Ala Glu Thr Met Gly Leu
            340                 345                 350

Asn Thr Ala Asp Thr Ala Arg Leu Asn Ala Asn Ile Arg Tyr Val Asn
            355                 360                 365

Thr Gly Thr Ala Pro Ile Tyr Asn Val Leu Pro Thr Thr Ser Leu Val
    370                 375                 380

Leu Gly Lys Asn Gln Thr Leu Ala Thr Ile Lys Ala Lys Glu Asn Gln
385                 390                 395                 400

Leu Ser Gln Ile Leu Ala Pro Asn Asn Tyr Tyr Pro Ser Lys Asn Leu
                405                 410                 415

Ala Pro Ile Ala Leu Asn Ala Gln Asp Asp Phe Ser Ser Thr Pro Ile
            420                 425                 430

Thr Met Asn Tyr Asn Gln Phe Leu Glu Leu Glu Lys Thr Lys Gln Leu
    435                 440                 445

Arg Leu Asp Thr Asp Gln Val Tyr Gly Asn Ile Ala Thr Tyr Asn Phe
450                 455                 460

Glu Asn Gly Arg Val Arg Val Asp Thr Gly Ser Asn Trp Ser Glu Val
465                 470                 475                 480

Leu Pro Gln Ile Gln Glu Thr Thr Ala Arg Ile Ile Phe Asn Gly Lys
                485                 490                 495

Asp Leu Asn Leu Val Glu Arg Arg Ile Ala Ala Val Asn Pro Ser Asp
            500                 505                 510

Pro Leu Glu Thr Thr Lys Pro Asp Met Thr Leu Lys Glu Ala Leu Lys
    515                 520                 525

Ile Ala Phe Gly Phe Asn Glu Ser Asn Gly Asn Leu Gln Tyr Gln Gly
530                 535                 540

Lys Asp Ile Thr Glu Phe Asp Phe Asn Phe Asp Gln Gln Thr Ser Gln
545                 550                 555                 560

Asn Ile Lys Asn Gln Leu Ala Glu Leu Asn Val Thr Asn Ile Tyr Thr
                565                 570                 575

Val Leu Asp Lys Ile Lys Leu Asn Ala Lys Met Asn Ile Leu Ile Arg
            580                 585                 590

Asp Lys Arg Phe His Tyr Asp Arg Asn Asn Ile Ala Val Gly Ala Asp
    595                 600                 605

Glu Ser Val Val Lys Glu Ala His Arg Glu Val Ile Asn Ser Ser Thr
610                 615                 620

Glu Gly Leu Leu Leu Asn Ile Asp Lys Asp Ile Arg Lys Ile Leu Ser
625                 630                 635                 640

Gly Tyr Ile Val Glu Ile Glu Asp Thr Glu Gly Leu Lys Glu Val Ile
                645                 650                 655

Asn Asp Arg Tyr Asp Met Leu Asn Ile Ser Ser Leu Arg Gln Asp Gly
            660                 665                 670

Lys Thr Phe Ile Asp Phe Lys Lys Tyr Asn Asp Lys Leu Pro Leu Tyr
    675                 680                 685

Ile Ser Asn Pro Asn Tyr Lys Val Asn Val Tyr Ala Val Thr Lys Glu
```

```
                690              695              700
Asn Thr Ile Ile Asn Pro Ser Glu Asn Gly Asp Thr Ser Thr Asn Gly
705                      710              715                  720

Ile Lys Lys Ile Leu Ile Phe Ser Lys Lys Gly Tyr Glu Ile Gly
                725              730              735
```

<210> SEQ ID NO 2
<211> LENGTH: 2369
<212> TYPE: DNA
<213> ORGANISM: Bacillus anthracis

<400> SEQUENCE: 2

```
aatttcaata taatataaat ttaattttat acaaaaagga gaacgtatat gaaaaaacga    60
aaagtgttaa taccattaat ggcattgtct acgatattag tttcaagcac aggtaattta   120
gaggtgattc aggcagaagt taaacaggag aaccggttat taaatgaatc agaatcaagt   180
tcccaggggt tactaggata ctattttagt gatttgaatt ttcaagcacc catggtggtt   240
acttcttcta ctacagggga tttatctatt cctagttctg agttagaaaa tattccatcg   300
gaaaaccaat attttcaatc tgctatttgg tcaggattta tcaaagttaa gaagagtgat   360
gaatatacat ttgctacttc cgctgataat catgtaacaa tgtgggtaga tgaccaagaa   420
gtgattaata agcttctaa ttctaacaaa atcagattag aaaaggaag attatatcaa   480 ataaaaattc aatatcaacg agaaaatcct actgaaaaag gattggattt caagttgtac   540
tggaccgatt ctcaaaataa aaagaagtg atttctagtg ataacttaca attgccagaa   600
ttaaaacaaa atcttcgaa ctcaagaaaa agcgaagta aagtgctgg acctacggtt   660 ccagaccgtg acaatgatgg aatccctgat tcattagagg tagaaggata tacggttgat   720
gtcaaaaata aaagaacttt tcttcacca tggatttcta atattcatga aagaaagga   780 ttaaccaaat ataaatcatc tcctgaaaaa tggagcacgg cttctgatcc gtacagtgat   840
ttcgaaaagg ttacaggacg gattgataag aatgtatcac cagaggcaag acacccctt   900 gtggcagctt atccgattgt acatgtagat atggagaata ttattctctc aaaaaatgag   960
gatcaatcca cacagaatac tgatagtcaa acgagaacaa taagtaaaaa tacttctaca  1020
agtaggacac atactagtga agtacatgga aatgcagaag tgcatgcgtc gttctttgat  1080
attggtggga gtgtatctgc aggatttagt aattcgaatt caagtacggt cgcaattgat  1140
cattcactat ctctagcagg ggaaagaact tgggctgaaa caatgggttt aaataccgct  1200
gatacagcaa gattaaatgc caatattaga tatgtaaata ctgggacggc tccaatctac  1260
aacgtgttac caacgacttc gttagtgtta ggaaaaaatc aaacactcgc gacaattaaa  1320
gctaaggaaa accaattaag tcaaatactt gcacctaata attattatcc ttctaaaaac  1380
ttggcgccaa tcgcattaaa tgcacaagac gatttcagtt ctactccaat tacaatgaat  1440
tacaatcaat ttcttgagtt agaaaaaacg aaacaattaa gattagatac ggatcaagta  1500
tatgggaata tagcaacata caattttgaa atggaagag tgagggtgga tacaggctcg  1560
aactggagtg aagtgttacc gcaaattcaa gaaacaactg cacgtatcat ttttaatgga  1620
aaagatttaa atctggtaga aaggcggata gcggcggtta atcctagtga tccattagaa  1680
acgactaaac cggatatgac attaaaagaa gcccttaaaa tagcatttgg atttaacgaa  1740
tcgaatggaa acttacaata tcaagggaaa gacataaccg aatttgattt taatttcgat  1800
caacaaacat ctcaaaatat caagaatcag ttagcggaat taaacgtaac taacatatat  1860
actgtattag ataaaatcaa attaaatgca aaaatgaata ttttaataag agataaacgt  1920
```

-continued

```
tttcattatg atagaaataa catagcagtt ggggcggatg agtcagtagt taaggaggct    1980
catagagaag taattaattc gtcaacagag ggattattgt taaatattga taaggatata    2040
agaaaaatat tatcaggtta tattgtagaa attgaagata ctgaagggct taaagaagtt    2100
ataaatgaca gatatgatat gttgaatatt tctagtttac ggcaagatgg aaaaacattt    2160
atagatttta aaaatataa tgataaatta ccgttatata taagtaatcc caattataag    2220
gtaaatgtat atgctgttac taaagaaaac actattatta atcctagtga gaatggggat    2280
actagtacca acgggatcaa gaaaatttta atcttttcta aaaaaggcta tgagatagga    2340
taaggtaatt ctaggtgatt tttaaatta                                      2369
```

<210> SEQ ID NO 3
<211> LENGTH: 30
<212> TYPE: PRT
<213> ORGANISM: Bacillus anthracis

<400> SEQUENCE: 3

```
Ser Glu Val His Gly Asn Ala Glu Val His Ala Ser Phe Phe Asp Ile
1               5                   10                  15

Gly Gly Ser Val Ser Ala Gly Phe Ser Asn Ser Asn Ser Ser
            20                  25                  30
```

<210> SEQ ID NO 4
<211> LENGTH: 30
<212> TYPE: PRT
<213> ORGANISM: Bacillus anthracis

<400> SEQUENCE: 4

```
Asp Gly Ile Pro Asp Ser Leu Glu Val Glu Gly Tyr Thr Val Asp Val
1               5                   10                  15

Lys Asn Lys Arg Thr Phe Leu Ser Pro Trp Ile Ser Asn Ile
            20                  25                  30
```

<210> SEQ ID NO 5
<211> LENGTH: 30
<212> TYPE: PRT
<213> ORGANISM: Bacillus anthracis

<400> SEQUENCE: 5

```
Thr Phe Leu Ser Pro Trp Ile Ser Asn Ile His Glu Lys Lys Gly Leu
1               5                   10                  15

Thr Lys Tyr Lys Ser Ser Pro Glu Lys Trp Ser Thr Ala Ser
            20                  25                  30
```

<210> SEQ ID NO 6
<211> LENGTH: 30
<212> TYPE: PRT
<213> ORGANISM: Bacillus anthracis

<400> SEQUENCE: 6

```
Ser Ser Pro Glu Lys Trp Ser Thr Ala Ser Asp Pro Tyr Ser Asp Phe
1               5                   10                  15

Glu Lys Val Thr Gly Arg Ile Asp Lys Asn Val Ser Pro Glu
            20                  25                  30
```

<210> SEQ ID NO 7
<211> LENGTH: 30
<212> TYPE: PRT
<213> ORGANISM: Bacillus anthracis

<400> SEQUENCE: 7

Gly Arg Ile Asp Lys Asn Val Ser Pro Glu Ala Arg His Pro Leu Val
1               5                   10                  15

Ala Ala Tyr Pro Ile Val His Val Asp Met Glu Asn Ile Ile
            20                  25                  30

<210> SEQ ID NO 8
<211> LENGTH: 30
<212> TYPE: PRT
<213> ORGANISM: Bacillus anthracis

<400> SEQUENCE: 8

Ser Ala Gly Phe Ser Asn Ser Asn Ser Ser Thr Val Ala Ile Asp His
1               5                   10                  15

Ser Leu Ser Leu Ala Gly Glu Arg Thr Trp Ala Glu Thr Met
            20                  25                  30

<210> SEQ ID NO 9
<211> LENGTH: 30
<212> TYPE: PRT
<213> ORGANISM: Bacillus anthracis

<400> SEQUENCE: 9

Ala Gly Glu Arg Thr Trp Ala Glu Thr Met Gly Leu Asn Thr Ala Asp
1               5                   10                  15

Thr Ala Arg Leu Asn Ala Asn Ile Arg Tyr Val Asn Thr Gly
            20                  25                  30

<210> SEQ ID NO 10
<211> LENGTH: 30
<212> TYPE: PRT
<213> ORGANISM: Bacillus anthracis

<400> SEQUENCE: 10

Asn Ala Asn Ile Arg Tyr Val Asn Thr Gly Thr Ala Pro Ile Tyr Asn
1               5                   10                  15

Val Leu Pro Thr Thr Ser Leu Val Leu Gly Lys Asn Gln Thr
            20                  25                  30

<210> SEQ ID NO 11
<211> LENGTH: 30
<212> TYPE: PRT
<213> ORGANISM: Bacillus anthracis

<400> SEQUENCE: 11

Leu Asn Ala Gln Asp Asp Phe Ser Ser Thr Pro Ile Thr Met Asn Tyr
1               5                   10                  15

Asn Gln Phe Leu Glu Leu Glu Lys Thr Lys Gln Leu Arg Leu
            20                  25                  30

<210> SEQ ID NO 12
<211> LENGTH: 30
<212> TYPE: PRT
<213> ORGANISM: Bacillus anthracis

<400> SEQUENCE: 12

Asn Ile Lys Asn Gln Leu Ala Glu Leu Asn Val Thr Asn Ile Tyr Thr
1               5                   10                  15

Val Leu Asp Lys Ile Lys Leu Asn Ala Lys Met Asn Ile Leu
            20                  25                  30

<210> SEQ ID NO 13
<211> LENGTH: 30
<212> TYPE: PRT
<213> ORGANISM: Bacillus anthracis

<400> SEQUENCE: 13

Ile Lys Leu Asn Ala Lys Met Asn Ile Leu Ile Arg Asp Lys Arg Phe
1               5                   10                  15

His Tyr Asp Arg Asn Asn Ile Ala Val Gly Ala Asp Glu Ser
            20                  25                  30

<210> SEQ ID NO 14
<211> LENGTH: 30
<212> TYPE: PRT
<213> ORGANISM: Bacillus anthracis

<400> SEQUENCE: 14

Gly Asp Leu Ser Ile Pro Ser Ser Glu Leu Glu Asn Ile Pro Ser Glu
1               5                   10                  15

Asn Gln Tyr Phe Gln Ser Ala Ile Trp Ser Gly Phe Ile Lys
            20                  25                  30

<210> SEQ ID NO 15
<211> LENGTH: 30
<212> TYPE: PRT
<213> ORGANISM: Bacillus anthracis

<400> SEQUENCE: 15

Leu Ser Gln Ile Leu Ala Pro Asn Asn Tyr Tyr Pro Ser Lys Asn Leu
1               5                   10                  15

Ala Pro Ile Ala Leu Asn Ala Gln Asp Asp Phe Ser Ser Thr
            20                  25                  30

<210> SEQ ID NO 16
<211> LENGTH: 30
<212> TYPE: PRT
<213> ORGANISM: Bacillus anthracis

<400> SEQUENCE: 16

Gly Tyr Ile Val Glu Ile Glu Asp Thr Glu Gly Leu Lys Glu Val Ile
1               5                   10                  15

Asn Asp Arg Tyr Asp Met Leu Asn Ile Ser Ser Leu Arg Gln
            20                  25                  30

<210> SEQ ID NO 17
<211> LENGTH: 30
<212> TYPE: PRT
<213> ORGANISM: Bacillus anthracis

<400> SEQUENCE: 17

Tyr Asn Asp Lys Leu Pro Leu Tyr Ile Ser Asn Pro Asn Tyr Lys Val
1               5                   10                  15

Asn Val Tyr Ala Val Thr Lys Glu Asn Thr Ile Ile Asn Pro
            20                  25                  30